United States Patent [19]

Brunner et al.

[11] Patent Number: 5,194,644
[45] Date of Patent: Mar. 16, 1993

[54] ETHYLENE-SUBSTITUTED PHENYLALKYLETHYLENE-DIAMINE-PLATINUM (II OR IV) DERIVATIVES AND PHENYLALKYLETHYLENEDIAMINES

[75] Inventors: Henri Brunner, Lappersdorf; Peter Hankofer, Cologne; Friedrich Maiterth, Hagelstadt; Jürgen Engel, Alzenau; Wolfgang Schumacher, Langen; Peter Hilgard, Bielefeld; Rainer Voegeli, Bielefeld, all of Fed. Rep. of Germany

[73] Assignee: Asta Pharma AG, Fed. Rep. of Germany

[21] Appl. No.: 683,431

[22] Filed: Apr. 10, 1991

[30] Foreign Application Priority Data

Apr. 10, 1990 [DE] Fed. Rep. of Germany ....... 4011520

[51] Int. Cl.$^5$ ............................................. C07F 15/00
[52] U.S. Cl. ...................................................... 556/137
[58] Field of Search ......................................... 556/137

[56] References Cited

U.S. PATENT DOCUMENTS

| | | | |
|---|---|---|---|
| 4,372,890 | 2/1983 | Yoshikumi et al. | 556/137 |
| 4,845,124 | 7/1989 | Kidani et al. | 556/137 |
| 4,921,984 | 5/1990 | Nowatari et al. | 556/137 X |
| 5,028,727 | 7/1991 | Verbeek et al. | 556/137 |
| 5,034,553 | 7/1991 | Verbeek et al. | 556/137 |

FOREIGN PATENT DOCUMENTS 0193083 2/1986 European Pat. Off. .

OTHER PUBLICATIONS

Article entitled "*Evidence of Delayed Internal . . .*", by S. Morgan et al. in the Journal of Amer. Chem. Soc. vol. 109 No. 10, pp. 3151-3154 1987 (May 13, 1987).
Article entitled "Synthesis and Characterization of a New Quinquedentate . . . " by Kanda et al., vol. 56, No. 11 Bull. Chem. Soc. Jpn., 56, 1983 (the chemical society of Japan) pp. 3268-3271.
Article entitled "Synthesis and Antitumor Activity . . . " by Burnner, et al. Nov. 30, 1989 Chemische Berichte pp. 1029-1038.
Chemical Abstracts Nov. 21, 1988 vol. 109 No. 21, 1988 p. 690.
Article entitled "Synthesis and Antitumor activity . . . " by Brunner et al. Eur. J. Med. Chem. (1990) 25,35-44.

*Primary Examiner*—Arthur C. Prescott
*Attorney, Agent, or Firm*—Cushman, Darby & Cushman

[57] ABSTRACT

Antitumor acting platinum(II or IV) complexes of the general formula

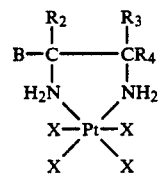

where B represents a phenyl-$C_1$-$C_4$-alkyl radical which is optionally substituted in the phenyl nucleus by the radical $R_1$ and $R_1$ is hydrogen, halogen, trihalogen methyl, $C_1$-$C_6$-alkyl, hydroxy, $C_1$-$C_6$-alkoxy or $C_2$-$C_6$-alkanoyloxy or where B together with the structural part $H_2N$—$CR_2$< forms a tetrahydroisoquinoline radical, if B contains benzyl and $R_2$ hydrogen and the benzyl radical in the 2-position contains the $CH_2$-radical or where B together with the structural part —$CR_2$< represents a tetrahydronaphthyl radical in which one $CH_2$ group is optionally replaced by oxygen, or where B together with the structural part —$CR_2$< represents a decahydronaphthyl radical or an indanyl radical; $R_2$ represents hydrogen, $C_1$-$C_6$-alkyl, phenyl or phenyl-$C_1$-$C_4$-alkyl, it also being possible for the phenyl ring of this group $R_2$ to be substituted by hydroxy, $C_1$-$C_4$-alkoxy, $C_1$-$C_4$-alkyl, $C_2$-$C_6$-alkanoyloxy or halogen; the radicals $R_3$ and $R_4$ are the same or different and represent hydrogen, $C_1$-$C_{12}$-alkyl, $C_3$-$C_8$-cycloalkyl and X stands for the equivalent of a physiologically acceptable anion or X can also be a water molecule, where in the latter case the missing negative charge is saturated by a corresponding physiologically acceptable acid anion, where in the case of platinum(II) complexes, two of the groups X are absent.

3 Claims, No Drawings

ETHYLENE-SUBSTITUTED PHENYLALKYLETHYLENE-DIAMINE-PLATINUM (II OR IV) DERIVATIVES AND PHENYLALKYLETHYLENEDIAMINES

The present invention relates to new ethylene-substituted phenylalkylethylenediamine-platinum(II or IV) derivatives and phenylalkylethylenediamines. These compounds are useful as tumor inhibiting agents.

BACKGROUND OF THE INVENTION

German published patent No. 36 05 191 describes anti-tumor acting (1-benzylethylenediamine)-platinum-(II) complexes of the general formula:

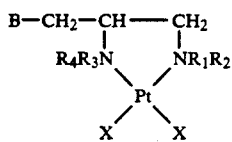

in which the radicals $R_1$, $R_2$, $R_3$ and $R_4$ are the same or different and represent hydrogen, a $C_1$–$C_6$-alkyl group, a benzyl group or a phenylethyl group, and B is a thienyl radical, an indolyl radical, an imidazolyl radical or a phenyl radical substituted by the radicals $R_5$, $R_6$ and $R_7$ and the radicals $R_5$, $R_6$ and $R_7$ are the same or different and represent hydrogen, halogen, trihalogen methyl, $C_1$–$C_6$-alkyl, hydroxy, $C_1$–$C_6$-alkoxy, phenoxy, benzyloxy, $C_1$–$C_6$-alkanesulfonyloxy, carboxy, carbalkoxy, cyano, aminocarbonyl, aminocarbonyl containing one or two $C_1$–$C_6$-alkyl radicals, $C_1$–$C_6$-alkylcarbonyl, nitro, amino, $C_1$–$C_6$-alkamino, di-$C_1$–$C_6$-alkylamino, ($C_1$–$C_6$-alkyl)$_3$N$^+$, $C_1$–$C_6$-alkanoyl-amino, $C_1$–$C_6$-alkyl-$C_1$–$C_6$-alkanoyl-amino, $C_1$–$C_6$-alkanesulfonylamino, $C_1$–$C_6$-alkyl-$C_1$–$C_6$-alkanoylamino, aminosulfonyl, aminosulfonyl containing one or two $C_1$–$C_6$-alkyl radicals, $C_1$–$C_6$-alkoxysulfonyl (—SO$_2$—O—C$_1$–C$_6$-alkyl), sulfo(—SO$_3$H) or $C_1$–$C_6$-alkanesulfonyl and two of these radicals can also be the methylenedioxy group and X stands for the equivalent of a physiologically acceptable anion.

SUMMARY OF THE INVENTION

The present invention relates to platinum(II or IV) complexes of the general formula:

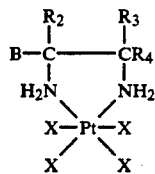

where B represents a phenyl-$C_1$–$C_4$-alkyl radical which is optionally substituted in the phenyl nucleus by the radical $R_1$ and $R_1$ is hydrogen, halogen, trihalomethyl, $C_1$–$C_6$-alkyl, hydroxy, $C_1$–$C_6$-alkoxy or $C_2$–$C_6$-alkanoyloxy or where B together with the structural part H$_2$N—CR$_2$< forms a tetrahydroisoquinoline radical, if B contains benzyl and $R_2$ is hydrogen and the benzyl radical in the 2-position contains the CH$_2$-radical or where B together with the structural part —CR$_2$< represents a tetrahydronaphthyl radical in which one CH$_2$ group is optionally replaced by oxygen, or where B together with the structural part —CR$_2$< represents a decahydronaphthyl radical or an indanyl radical; $R_2$ represents hydrogen, $C_1$–$C_6$-alkyl, phenyl or phenyl-$C_1$–$C_4$-alkyl, it also being possible for the phenyl ring of this group $R_2$ to be substituted by hydroxy, $C_1$–$C_4$-alkoxy, $C_1$–$C_4$-alkyl, $C_2$–$C_6$-alkanoyloxy or halogen; the radicals $R_3$ and $R_4$ are the same or different and represent hydrogen $C_1$–$C_{12}$-alkyl, $C_3$–$C_8$-cycloalkyl, phenyl which is optionally substituted by $C_1$–$C_6$-alkoxy and, if B is benzyl radical (optionally substituted as stated), at least one of the radicals $R_2$, $R_3$ and $R_4$ is not hydrogen and X stands for the equivalent of a physiologically acceptable anion or X can also be a water molecule, where in the latter case the missing negative charge is saturated by a corresponding physiologically acceptable acid anion, where in the case of platinum(II) complexes, two of the groups X are absent.

The present invention also relates to phenylalkylethylenediamine of the General Formula:

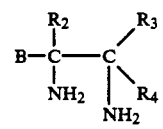

substituted in the ethylene part where B represents a phenyl-$C_1$–$C_4$-alkyl radical which is optionally substituted in the phenyl nucleus by the radical $R_1$ and $R_1$ is hydrogen, halogen, trihalogen methyl, $C_1$–$C_6$-alkyl, hydroxy, $C_1$–$C_6$-alkoxy or $C_2$–$C_6$-alkanoyloxy or where B together with the structural part H$_2$N—CR$_2$< forms a tetrahydroisoquinoline radical, if B contains benzyl and $R_2$ hydrogen and the benzyl radical in the 2-position contains the CH$_2$-radical or where B together with the structural part —CR$_2$< represents a tetrahydronaphthyl radical in which one CH$_2$ group is optionally replaced by oxygen, or where B together with the structural part —CR$_2$< represents a decahydronaphthyl radical or an indanyl radical; $R_2$ represents hydrogen, $C_1$–$C_4$-alkyl, phenyl or phenyl-$C_1$–$C_4$-alkyl, it also being possible for the phenyl ring of this group $R_2$ to be substituted by hydroxy, $C_1$–$C_4$-alkoxy, $C_1$–$C_4$-alkyl, $C_2$–$C_6$-alkanoyloxy or halogen, the radicals $R_3$ and $R_4$ are the same or different and represent hydrogen $C_1$–$C_{12}$-alkyl, $C_3$–$C_8$-cycloalkyl, phenyl which is optionally substituted by $C_1$–$C_6$-alkoxy and, if B is a benzyl radical (optionally substituted as stated), at least one of the radicals $R_2$, $R_3$ and $R_4$ is not hydrogen and salts thereof.

The following information relates to preferred embodiments of the invention:

The $C_1$–$C_6$-alkyl groups, $C_1$–$C_6$-alkoxy groups and the $C_1$–$C_6$-alkanoyloxy groups may be straight or branched. The alkyl or alkoxy groups preferably consist of 1 to 4 carbon atoms, the alkanoyloxy groups preferably of 2 to 4 carbon atoms. The alkanoyloxy group may in particular be the acetoxy group. The halogen substituents may in particular be bromine, chlorine and/or fluorine. In the case of the phenyl-$C_1$–$C_4$-alkyl group, the alkyl part preferably consists of one, two or three carbon atoms, preferably the benzyl group (phenylmethyl group) or the 1-phenylethyl group, the phenyl part optionally being substituted in each case as stated, the substituents preferably being in the 4-position.

A particular beneficial effect is displayed by those compounds of Formula I in which the radicals $R_3$ and $R_4$ are hydrogen or $C_1$–$C_4$-alkyl, in particular methyl and/or $R_2$ a $C_1$-$C_4$-alkyl group (in particular methyl or ethyl) a phenyl group or a phenyl group substituted by hydroxy (preferably p-hydroxy) and B represents a benzyl radical or a phenylethyl-(1)-radical where the phenyl ring of B is optionally substituted in particular by halogen (Cl) or hydroxy. This substituent (halogen or OH) is then preferably in the 4-position.

If B represents a phenyl-$C_1$-$C_4$-alkyl radical, this is preferably straight-chain, the phenyl group is preferably in the ω-position. The same also applies if $R_2$ represents phenyl-$C_1$-$C_4$-alkyl. The $C_3$-$C_8$-cycloalkyl group ($R_3R_4$) is preferably the cyclobutyl-, cyclopentyl-, cyclohexyl- or cycloheptyl group. Should there be platinum(IV)-complexes, 2 of the groups X preferably represent in each case OH or halogen (Cl, Br), whereas all the meanings given herefor are possible for the two other X. Should B together with the structural part $-CR_2<$ form a bicyclic ring, the following radicals are preferably involved: indanyl, preferably indanyl-(2) (see formula below); tetrahydronaphthyl, preferably tetrahydronaphthyl-(1) or tetrahydronaphthyl-(2) (see formula below); 1-oxa-tetrahydronaphthyl, preferably 1-oxa-tetrahydronaphthyl-(4), decahydronaphthyl, preferably decahydronaphthyl-(1).

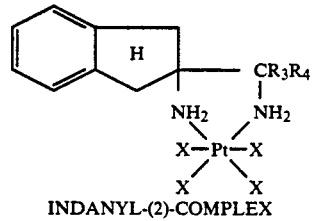
INDANYL-(2)-COMPLEX

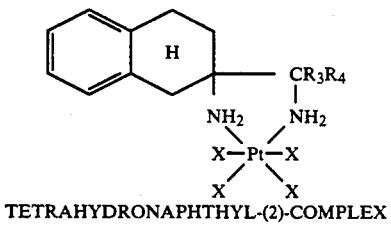
TETRAHYDRONAPHTHYL-(2)-COMPLEX (in the case of the oxa-tetrahydronaphthyl radical a $CH_2$ group of the bicyclic ring is replaced by an oxygen atom in the right hand formula: in the case of the decahydronaphthyl radical, the phenyl part of the bicyclic radical is also completely hydrated).

Should B together with the structural part $H_2N-CR_2<$ form a bicyclic ring (tetrahydroisoquinoline radical), these are compounds having the following structure:

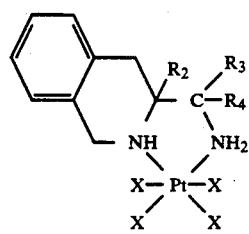

The radicals X, which may be the same or different, represent the known and conventional physiologically acceptable and pharmaceutically applicable anions of single or multivalent acids or also the hydroxy anion (OH$^-$). Should these acids have asymmetrical carbon atoms, these may be present as racemates, as optically pure forms or in the form of the corresponding diastereomers. The anions of the following acids may for example be considered in particular: HBr, HCl, HI, HF, $HNO_3$, $H_2SO_4$ ($SO_4^{--}$); $H_3PO_4$ ($HPO_4^{--}$); $H_2CO_3$, ($CO_3^{--}$); HSCN, camphorsulfonic acid, aliphatic or aromatic sulfonic acids, for example $C_1$-$C_6$-alkylsulfonic acids (for example methanesulfonic acid, ethane-, propane- or hexanesulfonic acid), benzene- or naphthalenesulfonic acid, which are optionally substituted once or twice by methyl groups (toluenesulfonic acid, in particular o- or p-toluenesulfonic acid), aliphatic $C_1$-$C_{20}$-monocarboxylic acids in particular $C_1$-$C_{18}$-monocarboxylic acids which are optionally substituted once, twice or three times by halogen atoms (in particular Cl, F) or also by a phenyl radical (in ω-position) (for example formic acid, acetic acid, propionic acid, palmitinic acid, stearic acid, chloroacetic acid, dichloroacetic acid, trifluoroacetic acid, trichloroacetic acid, ω-phenylstearic acid); aliphatic $C_2$-$C_{11}$-dicarboxylic acids which optionally contain a double bond (for example oxalic acid, malonic acid, 2-aminomalonic acid, malonic acid which is substituted in 2-position by a benzyl group or one or two $C_1$-$C_4$-alkyl groups, maleic acid, fumaric acid, succinic acid); aliphatic monohydroxy- and dihydroxymonocarboxylic acids with 2 to 8, in particular 2 to 6 carbon atoms, these preferably being α-monohydroxycarboxylic acids such as lactic acid, glyceric acid, mandelic acid or glycolic acid; di- and tricarboxylic acids with 3 to 8 carbon atoms, in particular 3 to 6 carbon atoms (for example malic acid, tartaric acid, malonic acid) which may also be substituted at a carbon atom by a hydroxy group and/or optionally a $C_1$-$C_4$-alkyl group (isocitric acid, citric acid); phthalic acid which is optionally substituted by a carboxyl group (in particular in 4-position); glutonic acid; glucuronic acid; azetidinecarboxylic acid; squaric acid (3,4-dihydroxy-3-cyclobutene-1,2-dione); the natural α-amino acids (for example L-asparaginic acid); 1,1-cyclobutanedicarboxylic acid; organophosphoric acids such as aldose- and ketosephosphoric acids (for example the corresponding mono- and diphosphoric acids) for example aldose-6-phosphoric acids such as D- or L-glucose-6-phosphoric acid, α-D-glucose-1-phosphoric acid, D-fructose-6-phosphoric acid, D-galactose-6-phosphoric acid, D-ribose-5-phosphoric acid, D-fructose-1,6-diphosphoric acids; glycerinephosphoric acids (where the phosphoric acid radical is bound to one of the terminal or to the central glycerol oxygen atom) such as α-D,L-glycerophosphoric acid, β-glycerophosphoric acid; N-phosphonoacetyl-asparaginic acid; nitrilotrismethylphosphonic acid.

X preferably represents chlorine, bromine, iodine or -SCN (rhodanide) or the anion X is derived from a hydroxycarboxylic acid of the structure $R_5$-CH(OH)-(CH$_2$)$_n$-CO$_2$H, where n can have the values 0, 1, 3 or 4 and $R_5$ represents hydrogen, halogen, hydroxy, $C_2$-$C_6$-alkanoyloxy, $C_1$-$C_6$-alkoxy, $C_1$-$C_6$-alkyl or phenyl which is optionally substituted by halogen, hydroxy, $C_1$-$C_6$-alkoxy, $C_1$-$C_6$-alkyl or $C_1$-$C_6$-alkanoyloxy.

In the case of an oxycarboxylic acid of this type, the complex part

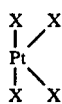

has the following structure

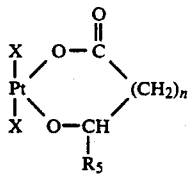

Two groups X are absent in the case of platinum(II) complexes or are preferably in each case OH, Cl or Br.

X is preferably derived from lactic acid, mandelic acid or glycolic acid (in each case racemate, D-form, L-form).

Acids that may also be considered for the anions X are: aromatic carboxylic acids which contain one or several carboxy groups as well as in addition also one or several (for example, one, two, three, four or five) $C_1$-$C_4$-alkoxy groups and/or hydroxy groups (for example salicylic acid). Should there by several carboxy groups at the aromatic radical (for example benzene ring), at least 2 carboxy groups are preferably located in adjacent ring positions. Should the benzene ring contain for example 4 or 5 carboxy groups, complexes may be formed which contain per 1 Mol of the benzenecarboxylic acid anion 2 Mol of the platinum component. Two adjacent ring carboxy groups neutralize in each case 1 Mol of the platinum component, with the result that for example in the case of the benzenepentacarboxylic acid, the 1- and 2-position as well as the 4- and 5-position carboxy groups in each case neutralize 1 Mol of the platinum component (thus 2 Mol together), whereas the free 3-position carboxy group is free or in the sale form with a physiologically acceptable cation (for example alkali cation, in particular sodium cation). This applies quite generally if the anions X possess additional acid functions, which are not used for neutralization of the platinum. The situation is analogous in the case of the benzenehexacarboxylic acid, where 1 Mol of this acid may optionally neutralize 3 Mol of the platinum component.

Examples of such acids are: benzenemonocarboxylic acid, benzenedicarboxylic acids, benzenetricarboxylic acids (for example trimellitic acid), benzenetetracarboxylic acids, benzenepentacarboxylic acid, benzenehexacarboxylic acid; syringic acid, orotic acid.

Acids which form the anions X, amino acids or amino acid derivatives, the basic amino group of which is protected by an acid group may also be considered. This may for example be amino acids of the following structure:

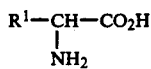

where $R^1$ represents hydrogen, a phenyl radical, an indolyl-(3)-methyl radical, imidazolyl-(4)-methyl radical, a $C_1$-$C_{10}$-alkyl group or a $C_1$-$C_{10}$-alkyl group which is substituted by a hydroxy group, an amino group, a carboxy group, a $C_1$-$C_6$-alkoxy group, a mercapto group, a $C_1$-$C_6$-alkylthio group, a phenyl group, a hydroxyphenyl group, a $C_2$-$C_6$-alkanoylamino group of a $C_1$-$C_6$-alkoxycarbonyl group.

The basic amino group in the 2-position is protected by a conventional amino acid protection group (acylated), for example by a $C_2$-$C_6$-alkanoyl radical, the benzoyl radical or the butyloxycarbonyl radical.

Should $R^1$ in the above formula be an alkyl group, this is preferably a $C_1$-$C_6$-alkyl group which contains for example in the 2-, 3-, 4-, 5- or 6-position (counting begins at the linkage point of the alkyl radical with the radical molecule) a $C_2$-$C_6$-alkanoylamino group, an imidazolyl-(4)-methyl radical or an indolyl-(3)-methyl radical. Individual examples of amino acids of this type are: leucine (preferably D- or L-form), valine (preferably D- or L-form), phenylalanine (preferably D- or L-form), phenylglycine (preferably D- or L-form), alanine (preferably D- or L-form), isoleucine (preferably D- or L-form), asparagine (preferably D- or L-form), lysine (preferably D- or L-form), tryptophan (preferably D- or L-form), tyrosine (preferably D- or L-form), ornithine (preferably D- or L-form), hydroxyproline (D- or L-form).

The basic amino groups in these acids may also be blocked by a conventional acylamino protective groups, such as the acetyl group, the chloroacetyl group, the benzoyl group of the butylcarbonyl group.

The corresponding acid addition salts may optionally also be prepared using physiologically acceptable acids, should the exchange groups X contain basic groups (for example amino groups).

Should X represent a water molecule, the stated acids may be considered, in particular strong acids, preferably $H_2SO_4$ for neutralizing the positive charge of the platinum atom.

Formulae I and II also comprise the possible enantiomers and diastereomers. Should the compounds be racemates, these may be split into the optically active isomers in manner known per se, for example by means of an optically active acid or by means of chiral phases. It is, however, possible to use, for the synthesis of such isomers, enantiomerically pure or optionally also diastereoisomerically pure starting materials, where the end product obtained is then a correspondingly pure optically active or diastereomeric compound. Independent of the structure of the radicals X, the platinum ligand also possesses asymmetrical carbon atoms and may therefore be present in the racemate form or in optically active or diastereomeric forms.

In the case of the platinum atom, the compounds of the invention of Formula I are in particular the cis-compounds.

The starting amine II is for example used as the racemate, as pure leavo or dextro-rotating form, as cis- or trans-form (with regard to the position of the aminomethyl groups) or in another diastereomeric form.

These configurations are retained during the preparation of the platinum complex.

The process for the preparation of the platinum(II) complexes of the invention of Formula I is carried out in a solvent at temperatures between 10° and 80° C., preferably 20° to 40° C., in particular 25° to 30° C. Solvents that may for example be considered are: water, $C_1$-$C_6$-alkanols (methanol, ethanol, tert.-butanol), cyclic ethers such as tetrahydrofuran, dioxane, saturated ethers of mono or multivalent alcohols such as ethyleneglycol dimethyl ether, diethyleneglycoldimethyl ether, lower saturated ketones (acetone, methylethyl ketone), aprotic agents such as dimethyl sulfoxide or dialkylamides of lower aliphatic carboxylic acids (formic acid, acetic acid) with $C_1$–$C_6$-alkyl radicals such as dimethylformamide, dimethylacetamide as well as mixtures of these solvents, in particular mixtures with water.

The two reaction components (platinum compound and compound II) are preferably used in equimolar amounts. The pH value of the reaction solution should be between 5 and 9, preferably at pH 6. The adjustment of the pH value is in particular achieved by addition of alkali, preferably aqueous sodium hydroxide solution or potassium hydroxide solution or for example also using sodium carbonate or through addition of acids, preferably aqueous hydrochloric acid. The pH may also be adjusted using ion exchangers.

Tetrahalogen-platinum(II) compounds (acid as well as complex salts) that may be considered are the corresponding tetrachloro-, tetrabromo- and tetraiodo-compounds. Should platinum(II) halides be used as starting components, the same halogen atoms may be considered.

Monovalent cations that may be considered are: alkali ions, in particular sodium and potassium; lithium, rubidium, caesium may, however, also be used, as may $NH_4^+$, $NR_4^+$, or $AsR_4^+$ in which R is a $C_1$–$C_6$-alkyl radical or a phenyl radical. Bivalent cations may be: alkaline earth ions, in particular $Mg^{2+}$ and $Ca^{2+}$, but also $Zn^{2+}$. Platinum(II) halides may for example be $PtCl_2$, $PtBr_2$ and $PtI_2$.

The compound II is either used in the form of the diamine or in the form of an acid addition salt: for example as monohydrochloride or dihydrochloride, mono- or dihydrobromide, mono- or dihydroiodide or as a salt with another conventional inorganic or organic acid. In particular it is also possible to consider those acids whose anions form the radicals X. In addition, the diamine may be used in the form of the acetate or diacetate, mixing optionally being preceded by addition of potassium chloride (for example 2 Mol per 1 Mol compound II) to the reaction components. Similarly, the diamine II may for example be used in the form of the hydrochloride, carbonate, oxalate or malonate.

The preparation of ethylenediamine ligands of Formula II is carried out, for example, by reduction of a compound of the formula

                    III or of their salts, where Z is either the cyano group or the group —$CONH_2$ or represents the group

and B and the radicals $R_2$, $R_3$ and $R_4$ have the meanings given above.

This process is carried out in a solvent or suspension agent at temperature which are for example between 20° to 150° C., preferably 40° to 150° C. Working may optionally also be under increased pressure (up to 150 bar). Solvents or suspension agents that may for example be considered are: water, symmetrical or unsymmetrical alkyl ethers with alkyl groups of 1-6 carbon atoms, saturated cycloaliphatic ethers such as tetrahydrofuran, dioxan, $C_1$–$C_6$-alkanols (methanol, ethanol, isopropanol), lower alkylamides or dialkylamides of aliphatic $C_1$–$C_2$-carboxylic acids, cyclic aliphatic acid amides (5- or 6-ring) such as N-methylpyrrolidone as well as mixtures of these agents.

Reduction agents that may be considered are: catalytically activated hydrogen using conventional metal catalysts (with and without carriers), such as precious metal catalysts (palladium, palladium on carbon, palladium on barium sulphate, platinum, platinum oxide, rhodium, ruthenium) or also nickel and cobalt catalysts, for example mixtures of such catalysts. The non-precious metal catalysts may also be used metalically on carriers (for example on $SiO_2$, Kieselguhr, $Al_2O_3$) or in particular in activated form (for example of the Raney type). The amount of catalyst may for example also be used in excess, for example 1-80%, preferably 2-40%, in particular 10-30% of the starting compound used. Solvents that may be used here are preferably polar agents, such as alcohols or alcohol-water mixtures. Reduction is, however, also possible with light metal hydrides, in particular complex light metal hydrides (sodium hydride, lithium hydride, lithium aluminum hydride, sodium triethoxyaluminum hydride, sodium bis-2-methoxyethoxy—aluminium dihydride, lithium tri-tert.-butoxyaluminium hydride and the like) alicyclic or cyclic ethers preferably being used as solvent at temperatures of preferably 20°-100° C.

Should the reduction be carried out with hydrogen as opposed to conventional hydrogenation catalysts, the process may also be carried out under pressure. Pressures of 1-300 bar, preferably 150 bar, in particular 70-100 bar may, for example, be considered.

Should the starting compounds of Formula III be nitriles or carboxylic acid amides (—$CONH_2$), reduction is preferably with a complex metal hydride (for example $LiAlH_4$) in a cyclic ether (tetrahydrofuran) at temperatures between 40°-100° C. or using hydrogen in the presence of a platinum catalyst. Should an azide be reduced as starting compound III, this reduction is preferably also with a complex metal hydride such as $LiAlH_4$ at temperatures between 10° and 50° C. (solvents in particular aliphatic optionally aqueous ethers such as for example moist diethyl ether).

Should the reaction occur with complex metal hydrides, hydrolysis is subsequently needed. This occurs for example with water or aqueous cyclic or non-cyclic ethers (for example diethylethers) at temperatures between 0°-30° C., preferably 0°-20° C., in particular 0°-5° C.

Diamine ligands of Formula II may also be prepared as follows: A ketone of general formula

where B, for example is phenylalkyl radical (e.g. phenylethyl) is cyclized in known manner with hydrocyanic acid and ammonium carbonate to a hydantoin of the general formula

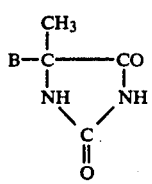

Temperature ranges
0°–50° C., preferably 20° C. for the addition of the hydrocyanic acid
10°–80° C., preferably 60° C. for the following reaction time Ring opening The ring opening in the autoclave preferably occurs without pressure (intrinsic pressure develops, a few bar) at temperatures of 100°–250° C., preferably 180° C.

Esterification with $SOCl_2$ as described for the preparation of the starting substances.

Preparation of the amide in the glass autoclave (or other metal autoclave) alcoholic (methanolic at best) solution, which is saturated with ammonia.

Temperature

−20° C. to +50° C. (preferably room temperature).

Reduction of the amide to diamine with $LiAlH_4$ (addition temperature for example −10° C.) in diethylether or tetrahydrofuran.

Precipitation of the amine preferably as oxalate or hydrochloride

Solvents that may be considered are alcohol/water mixtures or methanol/water.

Preparation of 5-methyl-5-phenethyl-hydantoin
=(5-methyl-5-phenethyl-imidazolin-2,4-dione)

A suspension of 144.1 g (1.5 Mol) ammonium carbonate in 800 ml methanol/water 1:1 mixture is prepared in a 2 liter three-necked flask. At a temperature of 20° C. 43.2 ml (1.1 Mol) hydrocyanic acid are added within 1 minute. 152.8 g (1.0 Mol) 4-phenyl-2-butanol (benzyl acetone) are then added dropwise, leading to a slight exothermic reaction (temperature increase to ca. 30° C.). The white emulsion is maintained at 40° C. for 1 hour and then for 2.5 hours at 60° C. The precipitate is suction filtered, washed twice with 50 ml methanol/-$H_2O$ 1:1 and dried in a vacuum at 60° C.

Yield: 212.3 g 97.3% of theory.
Melting point: 178°–179° C.

α-Methyl-homo-phenylalanine 54.6 g 5-methyl-5-phenethyl-hydantoin (0.25 Mol) are reacted with 30 g sodium hydroxide (0.75 Mol) and 150 ml water for 3.5 hours in an autoclave at an oil bath temperature of 180° C. After cooling, 350 ml $H_2O$ are added and the clear, light brown solution adjusted with hydrochloric acid to pH 7.0. The white precipitate is suctioned off, washed with 20 mg $H_2O$ and dried in a vacuum drying cabinet at 65° C. The produce is recrystallized twice from water.

Yield: 46.2 g 95.7% of theory.

α-Methyl-homo-phenylalanine-methyl ester 430 ml methanol are cooled to −10° C. in an ice/-sodium chloride mixture and reacted with 21.3 ml thionyl chloride (exothermic reaction). 44.5 g (0.23 mol α-methyl-homo-phenylalanine are added dropwise at room temperature. Boiling under reflux occurs for 8.5 hours, the mixture is concentrated in a rotary evaporator, taken up with $H_2O$ (350 ml) and reacted with 150 ml 25% $Nh_4OH$ solution. Extraction with dichloromethane occurs 5× and the combined extracts are dried over calcium carbonate and concentrated in a rotary evaporator. Yellowish oil.

Yield: 32 g 67% of theory.

α-Methyl-homo-phenylalanine amide 32 g α-methyl-homo-phenylalanine methyl ester (0.15 Mol) are reacted in a glass autoclave for 2 days with 2 liters saturated ammoniacal methanol solution at room temperature. The mixture is concentrated and the residue is washed with 300 ml diethylether. White crystals.

Yield: 18.6 g (62.68 of theory).

1-Phenethyl-1-methylethylenediamine oxalate 240 ml dry tetrahydrofuran are cooled to −10° C. in an ice/sodium chloride mixture. 10.96 g (0.289 Mol) lithiumaluminium hydride are carefully added at −10° C. 18.5 g amide are carefully added, stirred in the cold for 30 minutes and then heated to boiling point. After 6.5 hours the mixture is cooled to −10° C. and 19 ml acetic acid ethyl ester and then 41 ml water are carefully added dropwise. The mixture is suction filtered, washed with tetrahydrofuran and evaporated.

The amine is taken up in 100 ml absolute alcohol and precipitated as oxalate by reaction with 8.64 g oxalic acid.

Yield: 13.4 g.

the process for the preparation of platinum(IV) complexes of Formula I occurs for example in the same agents as for the process for preparing the platinum(II) complexes of Formula I. These reactions occur in a temperature range between 20° and 100° C., preferably 40°–80° C. Oxidation agents that may be considered are: halogens such as chlorine gas, bromine, iodine, hydrogen peroxide (for example 3 to 60%; preferably 10 to 40%, in particular 35%), dirhodan (gaseous), hydrohalic acids (HCl, HBr, HI). Should the oxidation occur with halogen, dirhodan or hydrohalic acids, the additional presence of a compound HX may not be necessary.

In the case of the platinum(IV) complexes, 2 radicals X are in each case preferably either halogen or hydroxy. In the case of the platinum(II) complexes, these are square-planar complexes; in the case of the platinum(IV) complexes, of the 2 new additional substituents X the one radical X is above, the other radical X below the plane.

The exchange of the ligands X against other ligands may for example occur by means of silver halide precipitation. For example, a dihaloplatinum(II or IV) compound of Formula I, in which X represents halogen (chlorine, bromine or iodine) is reacted in a solvent or suspension agent at temperatures between 0° to 90° C., preferably 10° to 50° C., in particular 30° to 40° C., preferably 40° C. with the silver salts of another acid which corresponds to the meaning X. It is, however, also possible to use silver nitrate as silver salt (for example aqueous solver nitrate solution) and, for example when the platinum complex of Formula I is a platinum-(II) complex, one obtains an ionic dihydro complex of formula

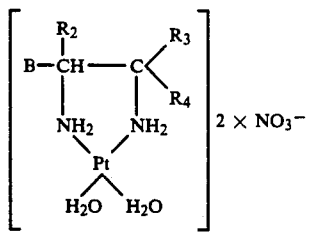

From this complex, the weakly bound ligand water can easily be displaced by anions with higher affinity (for example $Cl^-$, $Br^-$ in the form of NaCl, KCl, NaBr, KBr, $malonate^{2-}$, $chloroacetate^{(-)}$, $oxalate^{2-}$, 1,1-cyclobutane dicarboxylic acid $anion^{2-}$, glyconate, lactate and mandelate, as well as the remaining acid radicals X listed, used in the form of the acids or their salts, in particular their alkali salts.

The same compounds may also be obtained as follows: treatment of the previously mentioned dihydro nitrate complex with an anion exchanger in the hydroxide form (for example Dowex 1-8X), where the 2 molecules of water are replaced by OH and subsequent reaction of the complex compound so obtained (X=in each case OH) with the equimolar amount HX where X is a physiologically acceptable acid anion.

An exchange of the leaving group (for example $SO_4^{2-}$ or oxalate $anion^2$) is also possible in the case of the sulfato- or oxalato-platinum(II) compounds through reaction with alkaline earth salts which contain the desired X-ligands (for example glyceric acid), provided the complex formed is water soluble and thus permits the separation of the poorly water soluble alkaline earth sulfate or oxalate. X-ligands suitable for this process are preferably the anions of hydroxycarboxylic acids, sulfonic acids, haloacetic acids, nitric acid.

The solvents or suspension agents which are quoted for the method of preparation of compounds I may also be considered for the exchange reaction (the following are particularly suitable: water, dimethyl formamide, dimethyl acetamide, dimethyl sulfoxide, methanol, ethanol, tert.-butanol, acetone, methylethyl ketone). The exchange reaction is for example carried out in a pH range between 3 and 9.

Water solubility or solubility in physiologically acceptable agents or mixtures thereof among themselves and/or with water (aqueous NaCl, polyethylene glycols) of the platinum compounds of the invention may be improved through the use of solution promoting additives. These solubilizers are for example cyclodextrines, polyvinylpyrrolidone as well as non-ionic emulsifiers which are known under the trade mark Cremophor ® (see H. P. Fiedler, Lexikon der Hilfsstoffe für Pharmazie, Kosmetic und angrenzende Gebiete dated 1971, Published by Cantor/Aulendorf in Württemberg, page 132-134).

This yields genuine solutions or optionally also suspensions or emulsions.

Cyclodextrins are cyclic oligosaccharides which are obtained by enzymatic degradation of starch. The main degradation products isolated are $\alpha$-, $\beta$- and $\gamma$-cyclodextrin, in which six ($\alpha$), seven ($\beta$) or eight ($\gamma$) D-($\alpha$)-glucopyranose units are linked in their chair-form as $\alpha$-1,4-glycosides and which have an interstice. This interstice is available for the binding of nonpolar substrates which become water soluble through inclusion in the hydrophilic sheath. The cavity has a diameter of 0.45 nm for $\alpha$-cyclodextrin, 0.7 nm for $\beta$-cyclodextrin and 0.8–0.9 nm for $\gamma$-cyclodextrin.

In the case of the platinum complexes a part of the molecule has to penetrate the interstice in order to ensure solution promotion. For a preparation of this kind, the platinum complex of the invention is for example dissolved in ethanol and combined with the aqueous solution of the cyclodextrin. The solvent is then removed again. The remaining glassy residue is then water soluble after drying.

In the case of platinum complexes which are poorly soluble or even insoluble in ethanol or other organic solvents, the aqueous $\alpha$-cyclodextrin solution is for example added to the suspension of the platinum complex and the mixture so obtained is heated in a water bath to 60° C. until a clear solution is formed.

The solubilities obtained are for example set out in the following table.

Table

The quoted amounts are totally soluble in 10 ml solvent mixture consisting of 1.8% NaCl solution and polyethylene glycol 400 (1:1).

| The use of $\alpha$-cyclodextrin in double equivalent amount to the platinum complex | | |
|---|---|---|
| Compound According to example | without cyclodextrin | with cyclodextrin 2:1 |
| 2 | 6 mg | 18 mg |

This solvent mixture was selected because it is used for example in the application in the in vivo experiments.

Increase in the proportion of PEG in the solvent mixture improves dissolution behavior. For physiological reasons, however, this is not possible for the preparations to be applied.

The quantity ratio of cyclodextrin and platinum complex is preferably 2:1.

Polyvinylpyrrolidone

Polyvinylpyrrolidone (PVP) is a water-soluble polymer that is used in pharmaceutical technology inter alia as a viscosity increasing substance, as gel former and tabletting adjuvant. Polyvinylpyrrolidones having molecular weights of 5000 to 400000 may be considered.

Coprecipitates are formed together with the platinum complexes of the invention. To prepare these, the platinum complex is first dissolved, this being in ethanol or another organic solvent. The solution of the platinum complex is then mixed with the ethanolic PVP solution and the solvent drawn off.

The PVP chains prevent the development of interactions between the platinum complex molecules, with the result that a yellowish glass is formed in which the complex is distributed in the PVP matrix.

The platinum complex is present in unchanged form in the PVP matrix. The anion X (leaving group) is not exchanged during the coprecipitation.

The following table lists for example the amounts of platinum complex which may for example be dissolved as coprecipitate in 10 ml 1.8% sodium chloride solution/polyethylene glycol 400 (1:1).

Table

The quoted amounts are completely soluble in 10 ml solvent mixture composed of 1.8% NaCl solution and polyethylene glycol 400 (1:1).

| Use of PVP in a ratio of 50:1 to the platinum complex | | |
|---|---|---|
| Compound according to example | without PVP | as coprecipitate |
| 10 | 8.5 mg | 18 mg |
| 11 | 4.5 mg | 18 mg |
| 12 | no solution | <5 mg |
| 2 | 10 mg | <18 mg |

The ratio of PVP to platinum complex is selected for the precipitate in such a way that there are 50 monomeric units of PVP to 1 platinum complex molecule. The PVP selected had an average molecular weight of 10,000.

The preparation of solutions, suspensions or emulsions of the platinum(II) complexes of the invention using the solubilizers occurs for example by heating the components to temperatures between 40° and 100° C., preferably 50°-80° C., optionally with stirring or shaking or by means of ultrasound in water or a conventional organic solvent (in particular ethanol) or mixtures hereof. The solvent may then be removed by drawing off under vacuum or evaporation. This is for example necessary if the solvent/solvent mixture is not physiologically acceptable. The residue obtained is then taken up again optionally with stirring, shaking or with ultrasound into a physiologically acceptable solvent or suspension agent optionally with heating to 40°-100° C., preferably 40°-80° C.

The compounds of the invention possess tumor inhibiting properties and are suitable for the chemotherapy of tumour disorders. For example, in lymphatic leukemia P 388 in the female mouse, the compounds of the invention achieve a median survival time expressed in percent (% T/C, definition, see below) of over 125%, for example of 200-300%. Complexes of the compounds of the invention with haematoporphyrin show for example in P 388/leukemia a high anti-tumor effect at $1 \times 10^{-5}$ to $4 \times 10^{-5}$ Mol/kg body weight mouse.

The investigation for anti-tumour effect in P 388 leukemia in the mouse is carried out using the following method: lymphatic leukemia P 388 was established at the National Cancer Institute in the U.S.A. in 1955. The tumor line was induced through local application of methyl cholanthrene in DBA/2 mice and transferred in the first passage into the ascites form. (Dawe, Potter, Am. Ass. Scientific Proceedings; Pathologists and Bacteriologists, 33 (1957), 603).

The strain is maintained in female DBA/2 mice. Since the mean survival time of this tumor is only about ten days, the tumor strain has to be transplanted weekly. For this purpose, the tumor-carrying animal is killed by breaking its neck and the milky-cloudy ascites removed under sterile conditions by means of abdominal puncture. The tumor cells are diluted with sterile-filtered, ice-cold PBS solution (phosphate buffered saline) to a cell count of $1 \times 10^6 / 0.1$ ml injection volume and implanted intraperitoneally into 6-10-week-old animals.

The substances are tested in female $CD_2F_1$ mice (Zentralinstitut für Versuchstiere, Hannover) of body weight 17-21 g aged between 6-10 weeks. The tumor is removed on day 0 as described for strain maintenance and transplanted. Subsequently the animals are randomized in groups of size mice each.

On the following day (day 1) and on day 5 and day 9 (abbreviated $d_1$, $d_5$, $d_9$) the substances to be tested are administered in three different concentrations ($1 \times 10^6$ Mol/kg; $2 \times 10^6$ Mol/kg and $4 \times 10^{-5}$ Mol/kg to each group (i.e. per substance three groups applied according to body weight).

Per gram body weight of mouse, 0.01 ml of a solution are injected, containing in each case $1 \times 10^{-5}$, $2 \times 10^{-5}$ and $4 \times 10^{-5}$ Mol platinum complex in 10 ml, i.e. the amount for 1 kg mouse.

The parameter for the antitumour effect of a substance is taken to be the so-called median survival time of the test group in comparison to the untreated controls:

$$\frac{\text{mean survival time (test)}}{\text{mean survival time (controls)}} \times 100 = \% \ T/C$$

The following applies for mean survival time: with an even number of animals N:

$$\frac{x+y}{2},$$

where x is the day on which the number of dead animals is N/2 and y is the earliest day on which the number of dead animals is (N/2)+1.

with an uneven number of animals N: x

According to the NCI Protocol, a compound is considered to have anti-tumour activity if the T/C value is greater than 125%. Other information is obtained from the comparison of the animal weights on day 1 and day 5. The control animals gain 1.5-3 g in weight as a consequence of the growing ascites. Conversely, weight loss indicates toxic side effects. A substance is considered to be toxic in the given concentration if the weight loss is greater than 4 g or the T/C value is smaller than 85%.

The compounds of the invention show a good anti-tumor effect for example in P 388 leukaemia in the mouse (tumor implanatation intraperitoneal, treatment 1× intraperitoneal). For example in the above experimental method, a dose of 21.5 mg/kg body weight mouse prolonged survival time by 57%.

The minimum effective dose in the above animal experiment is for example 2 mg/kg oral
0.5 mg/kg sublingual
0.5 mg/kg intravenous The general dosage range for the effect (animal experiment as above) that may for example be considered is:

2-2000 mg/kg oral, in particular 50-500 mg/kg
0.5-1000 mg/kg intraperitoneal, in particular 3-100 mg/kg
0.5-1000 mg/kg intravenous, in particular 3-100 mg/kg The direction of effect of the compounds of the invention is comparable with the effect of the known pharmaceutically active ingredient cisplatin, carboplatin, although there are in particular the following differences thereto: compared to cisplatin: virtually no heophorotoxicity compared to carboplatin: substantially lower myelotoxicity and haemotoxicity Indications for which the compounds of the invention may be considered: chemotherapy of malignant diseases (cancer)

The pharmaceutical formulations contain in general between 1-2000, preferably 10-1000 mg of the active component(s) of the invention.

Administration may for example be in the form of tablets, capsules, pills, coated tablets, suppositories, ointments, gels, creams, powders, dusting powders, aerosols, lyophilisates, powders or in liquid form. Liquid forms of application that may for example be considered are: oily or alcoholic or aqueous solutions as well as suspensions and emulsions. Preferred forms of administration are tablets containing between 1 and 1000 mg, solutions containing 5 and 200 mg or lyophilisates containing between 5 and 400 mg, preferably 5 to 200 mg of the active substance.

The single dose of the active components of the invention lie a) in oral medicinal forms between 2 and 2000 mg, preferably 10–1000 mg.

b) inparenteral medicinal forms (for example intravenous, intramuscular) between 1 and 1000 mg, preferably 5–400 mg, in particular 5 to 200 mg.

c) in medicinal forms for rectal or vaginal application between 2 and 2000 mg, preferably 10–1000 mg.

d) in medicinal forms for local application to the skin and mucus membranes (for example in the form of solutions, lotions, emulsions, ointments and the like) between 0.01 and 10%, preferably 0.1 to 2%.

It is for example possible to recommend 3 times daily 1–4 tablets with a content of 10 to 500 mg active substance or for example in the case of intravenous injection 1 to 4 times daily one ampoule or injection bottle of 0.5 to 500 ml content with 1–200 mg substance. In the case of oral administration, the minimum daily dose is for example 1 mg; the maximum daily dose in oral administration should not exceed 2000 mg.

For the treatment of dogs and cats, the oral single dose generally lies between about 10 and 2000 mg/kg; the parenteral single dose about between 1 and 1000 mg/kg body weight.

The acute toxicity of the compounds of the invention in the mouse (expressed as the LD 50 mg/kg; method after Miller and Tainter: Proc. Soc. Exper. Biol. a. Med. 57 (1944) 261) lies for example with intraperitoneal application between 20 and 2000 mg/kg (depending on active substance).

The pharmaceuticals may be used in human medicine, in veterinary medicine and in agriculture alone or in mixture with other pharmacologically active substances.

(The doses are in each case related to the free base).

Preparation of the Starting Materials for the Phenylalkylethlenediamine LIGANDS

Starting Materials for C2-Substituted Phenylalkylethylenediamine

Working is based for example on an amino acid of the formula

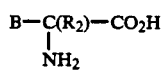

(for example phenylalanine or phenylalanine correspondingly substituted in the phenyl nucleus) and firstly esterifies these compounds in a manner known per se using thionyl chloride and methanol.

By means of the Grignard reaction the later substituents are introduced at the 2-position carbon atom of the benzylethylenediamine and the corresponding amino alcohols of formula

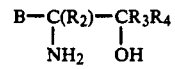

are obtained. The amino alcohol obtained in this manner can now be transferred into the aziridine with $Ph_3PBr_2$ and $Et_3N$ in acetonitrile by trans-elimination. For this purpose the reagent attaches itself onto the OH group of the alcohol and $Ph_3PO$ finally is eliminated with ring closure.

$Ph_3PBr_2$ for the reaction is prepared in situ from $Ph_3P$ and $Br_2$. Opening of the aziridine ring occurs with $NaN_3$ with formation of the amino azide which can then be reduced with $LiAlH_4$ to the diamine ligand. This route may be considered in particular if the radicals $R_3$ and $R_4$ are alkyl radicals.

Should the radicals $R_3$ and $R_4$ be for example phenyl, p-anisyl or cyclohexyl, i.e. non-linear radicals, it is advisable to effect direct substitution of the OH group through the azide group with the three-component system azodicarboxylic acid diethyl ester, triphenylphosphine and alcohol with addition of a fourth component HX. A betaine structure is formed from the triphenyl phosphine and the azo compound which highly activates the OH group of the alcohol component for the displacement so that substitution with the axide nucleophile can occur from the hydrazoic acid. The hydrozoic acid needed is used in the form of a toluene solution, the content of which must be determined in each case.

The aminoazide is finally isolated by first carefully suctioning off the solvent and transferring the residue to a silica gel column. Chromatography with ether-toluene 1:1 separates the reaction product in sufficiently pure form. The starting aminoazides thereby obtained have the following general formula:

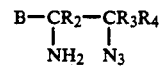

To obtain the diamine, reduction is carried out again with $LiAlH_4$. Examples of these reactions will be set out hereinbelow: D,L-phenylalanine methyl ester hydrochloride Ca. 150 ml methanol are prepared and 115 mMol (13.68 g; 8.3 ml) $SOCl_2$ added slowly with ice cooling using a dropping funnel. The 110 mMol (18.17 g) D,L-phenylalanine are added in solid form. The batch is heated for 24 hours under reflux. After removal of the solvent a colorless residue is obtained that is dried under high vacuum ($10^{-4}$ Torr). The ester hydrochloride is further processed without additional cleaning. Yield: quantitative.

By an analogous method one can obtain for example: 4-chlorophenylalanine methyl ester hydrochloride 4-methoxyphenylalanine methyl ester hydrochloride Grignard Reaction 0.1 Mol D,L-2-methyl-3-amino-4-phenylbutan-2-ol (2.43 g)

Mg turnings are covered with ether. About ⅓ of the 2M solution of 0.1 Mol (14.2 g; 6.2 ml) $CH_3I$ in ether are then added from the dropping funnel. The Grignard reaction can be initiated by gentle heating. With gentle stirring the remaining methyliodide solution is added dropwise in such a way that the mixture is maintained just at the boiling point. After everything has been added, heating to boiling is continued for about a further 30 minutes.

After cooling, 0.017 Mol (3.6 g) D,L-phenylalanine methyl ester hydrochloride are added in portions as a solid substance. The mixture is then heated to boiling for 15 hours.

Hydrolysis is achieved with a saturated solution of 0.17 Mol (9.1 g) $NH_4Cl$ in water. The solution is carefully filtered with vigorous stirring in order to remove the insoluble hydrolysis product and the filtrate is transferred to a separating funnel.

The organic phase is dried over $Na_2SO_4$ and then the solvent is suctioned off using a rotary evaporator. A colorless oil is obtained.

The aqueous phase is made ammoniacal with concentrated $NH_3$ and it is extracted with ether. After removal of the solvent an oily product is obtained. The oily residues from the organic and aqueous phase are distilled in a bulb tube in a high vacuum ($10^{-4}$ Torr) at 120° C. Yield: 70% colourless oil.

In an analogous manner, the Grignard reaction can be carried out using other alkyl halides, cycloalkyl halides or aromatic halocompounds (for example bromobenzene, bromoanisol and the like).

The Aziridine Route (D,L-2-Benzyl-3,3-Dimethyl Aziridine)

40 mMol (10.48 g) $Ph_3P$ are dissolved in 100 ml acetonitrile. 40 nMol (6.40 g; 2.06 ml) $Br_2$ in 40 ml acetonitrile are slowly added dropwise to this solution. 40 mMol (7.17 g) of the aminoalcohol, D,L-2-methyl-3-amino-4-phenylbutane-2-ol, are dissolved in ca. 100 ml acetonitrile and added dropwise to the $Ph_3PBr_2$ solution. Addition occurs with ice cooling.

80 mMol (8.08 g; 11.1 ml) $Et_3N$ in 10 ml acetonitrile are slowly added dropwise to this mixture with stirring. After a short period a colorless precipitate of $[Et_3NH]^+[Br]^-$ appears.

After the mixture has been left to stand overnight, the triethylamine hydrobromide is filtered off and the filtrate is concentrated in a rotatary evaporator.

The residue is transferred to a liquid/liquid extractor and is extracted for 24 hours with 250 ml hexane. The precipitate of triethylamine hydrobromide which forms is filtered off and washed with hexane. The solvent is drawn off from the filtrate in a rotary evaporator and the residue is distilled in a bulb tube at 90° C. in a high vacuum ($10^{-4}$ Torr). Yield: 40% colorless oil.

Opening of the Aziridine to the Amino Azides (D,L-1-phenyl-2-amino-3-azido-3-methyl butane)

10 mMol (1.61 g) of the aziridine are dissolved in 40 ml ethanol, mixed with 40 mMol (2.60 g) $NaN_3$ and 40 mMol (2,14 g) $NH_4Cl$ in 15 ml water and heated under reflux for 14–18 hours. The mixture is then diluted with water and shaken out with $CH_2Cl_2$. The organic phase is dried over $Na_2SO_4$ and the solvent is finally drawn off. Yield: 60% dark yellow oil.

The Azodicarboxylic Acid Diethyl Ester Route

Preparation of the Hydrazoic Acid 0.1 mMol (6.5 g) $NaN_3$ are taken up in 6.5 ml distilled water. 40 ml toluene are added to this solution. Following cooling of the mixture of 0° C., 5.16 ml concentrated $H_2SO_4$ (95%) is added dropwise in an ice bath in such a way that the temperature in the reaction vessel does not exceed +5° C.

After complete addition, the mixture is allowed to reach room temperature and is transferred to a separating funnel in order to separate off the aqueous phase. The toluene phase is dried over $Na_2SO_4$. The $HN_3$ content of the toluene solution is determined titrimetrically with 0.1N NaOH.

D,L-1,1-Dicyclohexyl-1-Azido-2-Amino-3-Phenyl Propane 22 mMol (3.89 g) azodicarboxylic acid diethyl ester dissolved in 20 ml toluene are added dropwise from the dropping funnel to a solution of 22 mMol (5.77 g) $Ph_3P$ and 20 mMol (6.4 g) D,L-1,1-dicyclohexyl-2-amino-3-phenylpropan-1-ol in 100 ml toluene. After addition of 22 mMol $HN_3$ in toluene solution, a colorless precipitate is formed. The mixture is stirred at room temperature for 15 hours, after which the precipitate is filtered off and the solvent suctioned off.

The brownish oil which is obtained as residue is again dissolved in a little toluene and applied to a silica gel column (50 cm×5 cm). After the substance has flowed into the column a chromatograph is taken with toluene/ether (1:1). The eluate is collected in four portions of ca. 70 ml each.

After the solvent has been drawn off, the IR spectra of fractions 3 and 4 show the azide bands of the aminoazide compound. Yield: 30% brownish-yellow oil.

The preparation of other 1-azido-2-amino-3-phenyl propanes with 2 substituents (for example 2 optionally substituted phenyl radicals) in 1 position is conducted in analogous manner.

Starting Materials for C1-substituted Phenylalkyl Ethylenediamines

Starting from the corresponding phenylalkyl ketones, the amino nitriles may be prepared and isolated in conventional manner therefor in a Strecker synthesis with NaCN and $NH_4Cl/NH_3$.

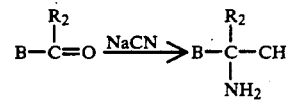

After completion of the reaction, the produce is isolated by adjusting the pH of the mixture to 6 using 1N HCl and the aminonitrile is then converted to its hydrochloride. The ketone which is still present can then be extracted with ether before the amine is released with ammonia, which can now also be extracted with ether.

After hydrolysis, the reduction of the amino nitrile with $LiAlH_4$ provides the corresponding diamines. This reduction also leads to a by-product in all cases. However, the desired diamine can be obtained in analytically pure form by means of simple bulb-tube distillation.

General Instructions for the Preparation of the Cis-Diamine Dichloro-Platinum(II) Complexes of Formula I A: Method in water 5 mMol of the corresponding diamine (compound II) are dissolved in ca. 25 ml distilled water. The pH of the solution is adjusted to 6 using 1N HCl. 5 mMol $K_2PtCl_4$ (2.08 g) are dissolved in 25 ml $H_2O$ and added to the neutral diamine solution with stirring. The batch is heated in a water bath to ca. 20° C. and the pH value is continuously monitored. If necessary, the mixture is adjusted to pH 6 with 1N NaOH. The reaction is regarded as complete, if the pH time remains virtually unchanged with time. The complex precipitates out as a fine crystalline precipitate and is filtered off (for example using a membrane filter frit). The mixture is then washed with water and a little ethanol and finally dried under a high vacuum ($10^{-4}$ Torr). The reaction product can for example be recrystallized by dissolving 50 mg thereof in 10 ml hot acetonitrile, then cooling to room temperature and finally in a deep freeze to $-10°$ C.

B: Method in water/tertiary butanol 0.5 mMol of the corresponding diamine are diluted in 50 ml tertiary butanol by adding a solution of 0.5 mMol $K_2PtCl_4$ in 5 ml water. A precipitate is formed which dissolves after addition of a further 25 ml of water. The solution so formed is neutralized with 1N HCl. After some time (for example after 30 minutes) the reaction product (platinum complex) separates off. After some hours (for example 3 hours) the precipitate is suctioned off and dried and optionally recrystallized, as set out under A.

EXAMPLE 1

D,L-1-(4-Chlorobenzyl)-2,2-dimethylethylenediaminedichloro-platinum(II)

Method A

Yield: 76%, pale yellow powder; M.P. >300° C. (disintegration) $C_{11}H_{17}Cl_3N_2Pt$ (molecular weight 478.7 g).

IR (KBr): 3240, 3110 cm$^{-1}$ (NH), 3040 (CH arom.), 2980 (CH aliph.), 1580 (NH), 330, 320 (PtCl).

1H-NMR ([D$_7$]DMF, 250 MHz): $\delta = 7.34$–7.44 (AA'BB', 4H, phenyl), 5.43 (m, 4H, NH$_2$), 3.13 (m, 1H, CH—N), 2.73–3.00 (m, masked by solvent signals, CH$_2$-phenyl), 1.49 (s, 3H, CH$_3$), 1.40 (s, 3H, CH$_3$).

(The letters AA'BB', AB stand for coupling patterns for various proton groupings)

| Analysis:   | C     | H    | N    |
|-------------|-------|------|------|
| calculated: | 27.60 | 3.58 | 5.85 |
| found:      | 27.58 | 3.50 | 5.76 |

EXAMPLE 2

D,L-1-Benzyl-2,2-dimethylethylenediaminedichloro-platinum(II)

Method A

Yield: 37%, pale yellow needles; M.P. >300° C. (disintegration) $C_{11}H_{18}Cl_2N_2Pt$ (molecular weight 444.3 g).

IR (KBr): 3190, 3110 cm$^{-1}$ (NH), 3020 (CH arom.), 2980 (CH aliph.), 1570 (NH), 300 (PtCl).

1H-NMR (CD$_3$CN, 250 MHz): $\delta = 7.21$–7.29 (m, 5H, phenyl), 4.72, 4.44, 4.26 4.07, 3.91 (5m, 4H, NH$_2$), 3.21 (m, 1H, $^3I_{CH-CH}=3.8$, $^3I_{CH-CH}=11.0$, $^3I_{CH-NH}=3.8$, $^3I_{CH-NH}=18.0$, CH—N), 2.88 (AB, 1H, $^2I=14.3$, CH-phenyl), 2.61 (AB, 1H, CH-phenyl), 1.40 (s, 3H, CH$_3$), 1.31 (s, 3H, CH$_3$).

| Analysis:   | C     | H    | N    |
|-------------|-------|------|------|
| calculated: | 29.74 | 4.08 | 6.31 |
| found:      | 29.82 | 4.18 | 6.23 |

EXAMPLE 3

D,L-1-Benzyl-2,2-diethylethylenediaminedichloro-platinum(II)

Method A

Yield: 68%, pale yellow powder; M.P.>300° C. (disintegration) $C_{13}H_{22}Cl_2N_2Pt$ (molecular weight 472.3 g).

IR (KBr): 3190, 3120 cm$^{-1}$ (NH), 3030 (CH arom.), 2970 (CH aliph.), 1590 (NH), 330, 320 (PtCl).

1H-NMR ([D$_7$]DMF, 250 MHz): $\delta = 7.25$–7.49 (m, 5H, phenyl), 5.37, 5.40 (2m, 2m, 1H, NH$_2$), 5.20, 5.25 (2m, 1H, NH$_2$), 5.06, 5.11 (2m, 1H, NH$_2$), 4.28, 4.32 (2m, 1H, NH$_2$), 2.93–3.12 (m, 3H, CH$_2$-phenyl, CH—N), 1.95–2.23, 1.72–1.91 (2m, 4H, CH$_2$), 0.97–1.08 (2t, 6H, $^3I=7.6$, CH$_3$).

| Analysis:   | C     | H    | N    |
|-------------|-------|------|------|
| calculated: | 33.06 | 4.70 | 5.93 |
| found:      | 33.22 | 4.67 | 5.93 |

EXAMPLE 4

D,L-1-Benzyl-2,2-dipentylethylenediaminedichloro-platinum(II)

Method B

Yield: 37%, pale yellow powder; M.P.>300° C. (disintegration) $C_{19}H_{34}Cl_2N_2Pt$ (molecular weight 556.5 g).

IR (KBr): 3240, 3110 cm$^{-1}$ (NH), 3040 (CH arom.), 2960, 2940 (CH aliph.), 1580 (NH), 330, 320 (PtCl).

1H-NMR ([D$_7$])DMF, 250 MHz): $\delta = 7.17$–7.34 (m, 5H, phenyl), 5.54, 5.58 (2m, 1H, NH$_2$), 4.97, 3.69 (2m, 2H, NH$_2$), 3.48, 3.52 (2m, 1H, NH$_2$), 2.93–2.99 (m, 2H, $^2I=11.1$, $^3I=14.8$, CH-phenyl, CH—N), 2.45 (AB, 1H, CH-phenyl), 1.25–1.69 (m, 16H, CH$_2$), 0.95 (t, 3H, CH$_3$), 0.88 (t, 3H, CH$_3$).

| Analysis:   | C     | H    | N    |
|-------------|-------|------|------|
| calculated: | 41.01 | 6.16 | 5.04 |
| found:      | 41.43 | 5.93 | 4.66 |

EXAMPLE 5

D,L-1-Benzyl-2,2-dicyclohexylethylenediaminedichloro-platinum(II)

Method B

Yield: 32%, pale yellow powder; M.P.>300° C. (disintegration) $C_{21}H_{34}Cl_2N_2Pt$ (molecular weight 580.5 g). The complex can be precipitated out of the acetonitrile solution by adding ether at room temperature.

IR (KBr): 3200 cm$^{-1}$ (NH), 3040) (CH arom.), 2940. 2860 (CH-aliph.), 1610 (NH), 320 (PtCl).

| Analysis:   | C     | H    | N    |
|-------------|-------|------|------|
| calculated: | 43.45 | 5.90 | 4.83 |
| found:      | 43.15 | 4.60 | 5.13 |

EXAMPLE 6

D,L-1-Benzyl-2,2-diphenylethylenediaminedichloro-platinum(II)

5 mMol (1.51 g) D,L-1-benzyl-2,2-diphenylethylenediamine are mixed with enough 1N HCl to dissolve the semi-solid diamine. This solution is neutralized with 1N NaOH, whereupon a cloudy emulsion appears.

5 mMol (2.08 g) $K_2PtCl_4$, dissolved in 25 ml $H_2O$, are added to this emulsion. At a constantly maintained pH value of 6.5–7 stirring continues for ca. 5 hours until the precipitated complex can be filtered off.

The precipitate is washed with ether and distilled $H_2O$ and dried in a high vacuum ($10^{-4}$ Torr).

Yield: 56%, pale yellow powder; M.P. >300° C. $C_{21}H_{22}Cl_2N_2Pt$ (molecular weight 568.4 g).

IR (KBr): 3220, 3160 cm$^{-1}$ (NH) 3110 (CH arom.), 2960, (CH aliph.), 1580 (NH), 330, 320 (PtCl).

1H-NMR ([$D_7$]DMF, 250 MHz): δ=7.95–8.13 (m, 5H, phenyl), 7.33–7.56 (m, 10H, phenyl), 6.62 (m, 2H, $NH_2$), 4.94, 5.00 (2m, 1H, $NH_2$), 4.32–4.38 (2m, 1H, $NH_2$), 3.92 (m, 1H, $^3I$, $^3I$=14.8, CH—N), 3.26 (AB, 1H, $^2I$=11.1, CH-phenyl), 3.11 (AB, 1H, CH-phenyl).

| Analysis:   | C     | H    | N    |
|-------------|-------|------|------|
| calculated: | 44.36 | 3.90 | 4.93 |
| found:      | 44.13 | 4.11 | 4.83 |

EXAMPLE 7

D,L-1-Benzyl-2,2-di(4-methoxyphenyl)ethylenediaminedichloro-platinum(II)

Method B (reaction time ca. 5 hours)

Yield: 56%, pale yellow powder; M.P. >300° C. (disintegration) $C_{23}H_{26}Cl_2N_2O_2Pt$ (molecular weight 628.5 g).

IR (KBr): 3260, 3160 cm$^{-1}$ (NH), 3090 (CH arom.), 2960, 2940 (CH aliph.), 1610 1580 (NH), 330, (PtCl).

1H-NMR ($CDCl_3$ 250 MHz): δ=6.87–8.13 (AA'BB', 4H, phenyl), 7.23–7.32 (m, 5H, phenyl), 6.89–7.17 (AA'BB', 4H, phenyl), 6.11, 6.19 (2m, 1H, $NH_2$), 4.83, 4.79 (2m, 2H, $NH_2$), 3.97, 3.87 (2m, 1H, $NH_2$), 3.89, 3.80 (2s, 6H, $OCH_3$), 3.26 (AB, 1H, CH-phenyl), 2.46 (m, 1H, CH—N), 2.22 (AB, 1H, CH-phenyl).

| Analysis:   | C     | H    | N    |
|-------------|-------|------|------|
| calculated: | 43.95 | 4.17 | 4.46 |
| found:      | 44.49 | 4.54 | 4.19 |

EXAMPLE 8

D,L-1(4-Methoxybenzyl)-2,2-di(4-methoxyphenyl)ethylenediaminedichloro-platinum(II)

Method B (Precipitaiton of the reaction product as in Example 5)

Yield: 32% pale yellow powder; M.P. >300° C. (disintegration) $C_{24}H_{28}Cl_2N_2O_3Pt$ (molecular weight 658.5 g).

IR (KBr): 3240, 3180 cm$^{-1}$ (NH) 3100 (CH arom.), 2960, 2940 (CH aliph.), 1610, 1580 (NH), 330 (PtCl).

1H-NMR ($CDCl_3$, 250 MHz): δ=6.86–8.32 (AA'BB', 4H, phenyl), 7.01–7.29 (AA'BB', 4H, phenyl), 6.80–7.07 (AA'BB', 4H, phenyl), 6.14, 6.22 (2m, 1H, $NH_2$), 4.82, 4.79 (2m, 2H, $NH_2$), 3.95, 4.02 (2m, 1H, $NH_2$), 3.89, 3.80 (3s, 9H, $OCH_3$), 3.20 (AB, 1H, CH-phenyl), 2.46 (m, 1H, CH-N), 2.12 (AB, 1H, CH-phenyl).

EXAMPLE 9

D,L-1-Benzyl-1-phenylethylenediaminedichloro-platinum(II)

Method B

Yield: 62%, pale yellow powder; M.P. >300° C. (disintegration) $C_{15}H_{18}Cl_2N_2Pt$ (molecular weight 492.3 g).

IR (KBr): 3280, 3200 cm$^{-1}$ (NH) 3060 (CH arom.), 2960, 2920 (CH aliph.), 1610, 1580 (NH), 330, (PtCl).

1H-NMR ([$D_7$]DMF, 250 MHz): δ=7.59–7.64, 7.38–7.48, 7.08–7.34, 6.92–6.96 (4m, 10H, phenyl), 5.52–5.57 (m, 4H, $NH_2$), 3.65 (AB, 1H, $^2I$=13.4, CH-phenyl), 3.53 (AB, 1H, CH-phenyl), 3.13–3.30 (m, 2H, $CH_2$).

| Analysis:   | C     | H    | N    |
|-------------|-------|------|------|
| calculated: | 36.59 | 4.23 | 6.53 |
| found:      | 36.53 | 3.71 | 5.36 |

EXAMPLE 10

D,L-1-Benzyl-1-methylethylenediaminedichloro-platinum(II)

Method A

Yield: 73%, pale yellow powder; M.P. >300° C. (disintegration) $C_{10}H_{16}Cl_2N_2Pt$ (molecular weight 430.3 g).

IR (KBr): 3300, 3200 cm$^{-1}$ (NH), 3140 (CH arom.), 2660, 2940 (CH aliph.), 1610, 1580 (NH), 320, (PtCl).

1H-NMR ([$D_7$]DMF, 250 MHz): δ=7.26–7.42, (m, 5H, phenyl), 5.37, 6.07 (m, 2H, $NH_2$), 5.37, 5.41 (2m, 1H, $NH_2$), 5.02, 5.06 (2m, 1H, $NH_2$), 3.21 (s, 2H, $CH_2$-phenyl), 2.86–2.95, 2.53–2.58 (2m, 2H, masked by solvent signals, $CH_2$-N), 1.39 (s, 3H, $CH_3$).

| Analysis:   | C     | H    | N    |
|-------------|-------|------|------|
| calculated: | 27.92 | 3.75 | 6.51 |
| found:      | 28.11 | 3.66 | 6.42 |

EXAMPLE 11

D,L-1-Benzyl-1-ethylethylenediaminedichloro-platinum(II)

Method A

Yield: 54%, pale yellow powder; M.P. >300° C. (disintegration) $C_{11}H_{18}Cl_2N_2Pt$ (molecular weight 444.3 g).

IR (KBr): 3200, 3280 cm$^{-1}$ (NH), 3140 (CH arom.), 2960, 2940 (CH aliph.), 1610, 1580 (NH), 320, (PtCl).

1H-NMR ([$D_7$]DMF, 250 MHz): δ=7.46–7.56, 7.33–7.37 (2m, 5H, phenyl), 5.54, (m, 2H, $NH_2$), 5.08, 5.11 (2m, 1H, $NH_2$), 4.72, 4.77 (2m, 1H, $NH_2$), 3.33 (AB, 1H, $^2I$=13.8 CH-phenyl), 3.10 (AB, 1H, CH-phenyl), 2.72–2.76 (masked by solvent signals, 2H, $CH_2$-N), 1.67–1.86 (m, 2H, $CH_2$), 1.06, 1.12 (t, 3H, $^3I$=7.6, $CH_3$).

| Analysis:   | C     | H    | N    |
|-------------|-------|------|------|
| calculated: | 29.74 | 4.08 | 6.31 |
| found:      | 29.91 | 4.13 | 6.28 |

EXAMPLE 12

1,1-Dibenzyl-1-ethylethylenediaminedichloro-platinum(II)

Method A (Diamine soluble in water after gentle heating)

Yield: 63%, pale yellow powder; M.P. >300° C. (disintegration) $C_{16}H_{20}Cl_2N_2Pt$ (molecular weight 506.4 g).

IR (KBr): 3260, 3200 cm$^{-1}$ (NH) 3120 (CH arom.), 2960 (CH-aliph.), 1610, 1580 (NH), 330, (PtCl).

1H-NMR ([D$_7$]DMF, 250 MHz): δ=7.44–7.59, 7.31–7.43 (2m, 10H, phenyl), 5.60 (m, 2H, NH$_2$), 4.63 (m, 2H, NH$_2$), 3.37 (AB, 2H, $^2$I=13.7, CH$_2$-phenyl), 3.10 (AB, 2H, $^2$I=13.7, CH$_2$-phenyl), 2.67 (m, 2H, CH$_2$-N).

| Analysis: | C | H | N |
|---|---|---|---|
| calculated: | 37.95 | 3.98 | 5.53 |
| found: | 38.32 | 4.27 | 5.47 |

EXAMPLE 13

2-Amino-2-aminomethylindane dichloro-platinum(II)

Method A

Yield: 80%, pale yellow powder; M.P. >300° C. (disintegration) $C_{10}H_{14}Cl_2N_2Pt$ (molecular weight 428.2 g).

| | IR (KBr): | | | | | | |
|---|---|---|---|---|---|---|---|
| [cm$^{-1}$] | ν(NH) sym. and asym. | CH arom. | CH aliph. | δ(NH) | ν(C=C) sym. and asym. | CH arom. out of plane | ν PtCl |
| 13 | 3240s 3180m | 3050m | 2920w 2840 | 1590m 1580m | 1490m 1460m | 750s 800m | 310m |

| 1H-NMR ([D$_7$])DMF, 250 MHz): | | |
|---|---|---|
| d[ppm] | | Assignment |
| 7.25–7.15 | (m, | phenyl), |
| 5.74 | (m, | NH$_2$), |
| 3.38 | (s, | CH$_2$-indan), |
| 2.92 | (m, | CH$_2$), |

| Analysis: | C | H | N |
|---|---|---|---|
| calculated: | 28.05 | 3.30 | 6.54 |
| found: | 28.10 | 3.34 | 6.27 |

EXAMPLE 14

D,L-3-Aminomethyl-1,2,3,4-tetrahydroisoquinoline dichloro-platinum(II)

Method A

Yield: 65%, pale yellow powder; M.P. >300° C. (disintegration) $C_{10}H_{14}Cl_2N_2Pt$ (molecular weight 428.2 g).

| | IR (KBr): | | | | | | |
|---|---|---|---|---|---|---|---|
| [cm$^{-1}$] | (NH) sym. and asym. | CH arom. | CH aliph. | (NH) | (C=C) sym. and asym. | CH arom. out of plane | PtCl |
| 14 | 3260m 3200m | 3120s | 2960m 2860w | 1590m 1580m | 1500m 1460m | 760s 710w | 310m 330m |

| 1H-NMR ([D$_7$]DMF, 250 MHz): | | |
|---|---|---|
| [ppm] | | Assignment |
| 7.11–7.22 | (m, | phenyl), |
| 6.33 | (m, | NH$_2$, NH), |
| 5.57 | (m, | NH$_2$, NH), |
| 4.68 | (AB-syst. | CH$_2$, tetrahydroisoquinoline), |
| 4.54 | (AB-syst. | CH$_2$, tetrahydroisoquinoline), |
| 4.03–4.14 | (m, | CH-tetrahydroisoquinoline-N |
| 3.02–3.24 | (m, | CH—N/CH$_2$-tetrahydroisoquinoline-N) |

| Analysis: | C | H | N |
|---|---|---|---|
| calculated: | 28.05 | 3.30 | 6.54 |
| found: | 28.94 | 3.39 | 6.33 |

EXAMPLE 15

D,L-1-Amino-1-aminomethyltetralin dichloro-platinum(II)

Method A

Yield: 77%, yellow powder.

$C_{11}H_{16}Cl_2N_2Pt$ (molecular weight 442.3 g).

IR (KBr): 3280, 3220 cm$^{-1}$ (NH), 3060 (CH arom.), 2970, 2920 (CH aliph.), 1590 (NH), 320, (PtCl).

1H-NMR (DMF-d$_7$, 250 MHz): 7.30–7.14, (m, 4H, phenyl), 5.54 (m, 4H, NH$_2$), 3.75–3.68 (m, 2H, CH$_2$-phenyl), 2.71 (m, CH$_2$-N. masked by solvent signals), 2.29–1.28 (m, 4H, CH$_2$).

| Analysis: | C | H | N |
|---|---|---|---|
| calculated: | 29.87 | 3.65 | 6.34 |
| found: | 30.22 | 3.64 | 6.29 |

EXAMPLE 16

D,L-1-Amino-4-aminomethylchroman dichloro-platinum(II)

Method A

Yield: 52%, yellow powder.

$C_{10}H_{14}Cl_2N_2OPt$ (molecular weight 444.2 g).

IR (KBr):: 3240, 3200 cm$^{-1}$ (NH), 3070 (CH arom.), 2960 (CH aliph.), 1590 (NH), 320 (PtCl).

1H-NMR (DMF-d$_7$, 250 MHz): 7.28–6.81 (m, 4H, phenyl), 5.79, 5.64 (2m, 4H, NH$_2$), 4.48–4.20 (m, 2H, CH$_2$-O), 3.37–3.25 (m, 2H, CH$_2$-N), 2.78–2.73 (m, 2H, CH$_2$, masked by solvent signals).

| Analysis: | C | H | N |
|---|---|---|---|
| calculated: | 24.04 | 3:18 | 6.31 |
| found: | 27.39 | 3.20 | 6.09 |

D,L-2-Amino-2-aminomethyldecalin dichloro-platinum(II)

Method A

Yield: 62%, yellow powder.

$C_{11}H_{22}Cl_2N_2Pt$ (molecular weight 448.3 g).

IR (KBr): 3200 3140 cm$^{-1}$ (NH), 2920, 2860 (CH aliph.), 1580 (NH), 320 (PtCl).

1H-NMR (DMF-d$_7$, 250 MHz): 5.40–5.02 (3m, 4H, NH$_2$), 2.78, 2.73 (m, CH$_2$-N, 2H masked by solvent signals), 2.22–0.89 (m, 16H, CH, CH$_2$).

| Analysis: | C | H | N |
|---|---|---|---|
| calculated: | 29.47 | 4.95 | 6.25 |
| found: | 30.28 | 5.07 | 6.18 |

EXAMPLE 18

D,L-1-(p-Methoxy)benzyl-1-methylethylenediaminedichloro-platinum(II)

Method A

Yield: 68%, yellow needles, recrystallized from acetonitrile $C_{11}H_{18}Cl_2N_2OPt$ (molecular weight 460.3 g).

IR (KBr): 3260, 3210 cm$^{-1}$ (NH), 3050 (CH arom.), 2960, 2930 (CH aliph.), 1610, 1570 (NH), 320 (PtCl).

1H-NMR (DMF-d$_7$, 250MHz): 7.32–6.39 (AA′BB′, 4H, phenyl), 5.58–4.95 (4m, 4H, NH$_2$), 3.80 (s, 3H, CH$_3$-O), 3.15 (AB, 2H, CH$_2$-phenyl), 2.90–2.81 (m, CH$_2$-N, masked by solvent signals), 1.37 (s, 3H, CH$_3$).

| Analysis:   | C     | H    | N    |
|-------------|-------|------|------|
| calculated: | 28.70 | 3.94 | 6.09 |
| found:      | 28.78 | 4.00 | 6.05 |

EXAMPLE 19

D,L-2-Amino-2-aminomethyltetralin dichloro-platinum(II)

Method A

Yield: 39%, yellow needles.

$C_{11}H_{16}Cl_2N_2Pt$ (molecular weight 442.3 g).

IR (KBr): 3240, 3195 cm$^{-1}$ (NH), 3060 (CH arom.), 2950, 2910 (CH aliph.), 1580 (NH), 330 (PtCl).

1H-NMR (DMF-d$_7$, 250 MHz): 7.14 (m, 4H, phenyl), 5.54–5.47 (m, 4H, NH$_2$), 3.26 (AB, 2H, CH$_2$-phenyl), 3.07, 3.00 (m, 2H, CH$_2$-phenyl, masked by solvent signals), 2.45–2.40 (m, 2H, CH$_2$-N), 2.40–2.19 (m, 2H, CH$_2$).

| Analysis:   | C     | H    | N    |
|-------------|-------|------|------|
| calculated: | 29.87 | 3.65 | 6.34 |
| found:      | 30.42 | 4.05 | 6.24 |

EXAMPLE 20

1-(p-Hydroxy)benzyl-1-methylethylenediaminedichloro-platinum(II)

Method A

Yield: 57%, yellow needles.

$C_{10}H_{16}Cl_2N_2OPt$ (molecular weight 446.2 g). IR (KBr): 3350 cm$^{-1}$ (OH), 3270, 3250 (NH), 3020 (CH arom.), 2960, 2920 (CH aliph.), 1585, 1620 (NH), 360 (PtCl).

1H-NMR (DMF-d$_7$, 250 MHz): 9.51 )s, 1H, OH), 7.22–6.80 (AA′BB′, 4H, phenyl), 5.55–4.89 (m, 4H, NH$_2$), 3.09 (AB, 2H, CH$_2$-phenyl), 2.87–2.54 (m, 2H, CH$_2$-N, masked by solvent signals), 1.37 (s, 3H, CH$_3$).

EXAMPLE 21

Dichloro(1-phenethyl-1-methylethylenediamine)-platinum(II)

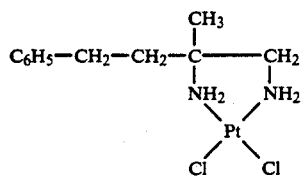

5 g (0.02 Mol) 1-phenethyl-1-methylethylenediamine oxalate are dissolved in 50 ml water with 4.5 KOH. A solution of 8.26 g (0.02 Mol) potassium tetrachloroplatinate in 50 ml H$_2$O is added thereto dropwise with stirring and stirring continued for 2 hours at 50° C.

The precipitate is suction filtered, washed with water and dried in a vacuum at 40° C.

Yellow powder, M.P. 298° C. (decomposition).

Yield: 6.21 g.

The glycolato complex (replacement of the 2 Cl by glycolic acid) is for example obtained as follows:

12.5 g chlorine complex are suspended with 9.56 g silver nitrate in 80 ml water and 8 ml ethanol. Stirring continues for several days at 45° C. with exclusion of light, the precipitate is suction filtered and the filtrate is mixed with 2.13 g (0.028 Mol) glycolic acid. After stirring for several days at room temperature the mixture is concentrated in a rotary evaporator, the residue is washed with diethyl ether and dried in a vacuum.

White powder, M.P. 219°–221° C. (decomposition). The compound contains 2 Mol water.

Yield: 9.5 g.

The D-lactato complex is obtained by analogy with the glycolate complex by using instead of the glycolic acid 12.6 g (0.028 Mol) D-lactic acid 20%. The workup is the same.

M.P. 206°–207° C. (decomposition). The compound contains 1 Mol water.

Yield: 9.8 g.

The preparation of the L-lactato complex is carried out by analogy with the D-lactato complex with 12.6 g (0.028 Mol) L-lactic acid b 20%.

White powder, M.P. 203°–204° C. (decomposition.

Yield: 10.5 g.

The preparation of the stearinato complex is carried out in a manner analogous to the lactato complex with 14.34 g (0.056 Mol) stearic acid.

Yellow Powder, M.P. 228C. (decomposition: substance D 21 393).

Yield: 8.3 g.

The preparation of the neodecanto complex is carried out in an analogous manner to the D-lactato complex with 0.056 Mol (9.6 g) neodecanic acid.

Yellow, pasty product (substance D 21 392).

Yield: 9.4 g; no melting point.

The ω-phenyloctadecanato(ω-phenyl-stearinato) complex is prepared by analogy with the D-lactato complex with 20.1 g (0.056 Mol) ω-phenyloctadecanic acid (ω-phenyl-stearinic acid).

Yellowish, slightly pasty solid (substance D 21 394).

Yield: 24 g; no melting point.

The sulphato complex is prepared by reaction of 2 g (0.0045 Mol) chloro complex with 1.25 g (0.004 Mol) silver sulphate in 800 ml water/100 ml ethanol mixture. The reaction time is 4 days at 45°–50° C. After suction filtering over a membrane filter, 2.1 g of a white product are obtained. (substance D 21 407).

M.P.: 243° C. (decomposition).

In a manner analogous to the preparation of the D-lactato complex, 10 g chloro complex (0.0225 Mol) are reacted with 5.9 g 0.045 Mol N-acetyl-L-alanine.

Yield: 5.8 g white powder (substance D 21 476).

M.P.: 225° C. (decomposition).

The complex still contains 1 Mol water.

The nitrolotris(methylphosphonato) complex is prepared in a manner analogous to the D-lactato complex by reaction with 0.056 Mol (16.7 g) nitrolotris-methylphosphonic acid.

White powder M.P.: 254° C. (substance D 21 569).
Yield: 7.8 g.
The complex has the following structure:

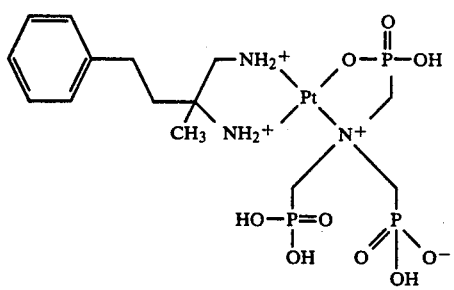

EXAMPLE 22

(Platinum(IV) complexes)

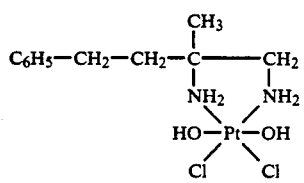

Dichloro-dihydroxy-(1-phenethyl-1-methylethylenediamine)-platinum(IV)

1 g Dichloro(1-phenethyl-1-methylethylenediamine)-platinum(II) (0.002 Mol) is suspended in 30 ml water. 10 ml 35% hydrogen peroxide solution are added dropwise at 70° C. They highly foaming suspension is stirred for 4 hours at 70° C. and a clear solution is obtained.

The excess $H_2O_2$ is carefully destroyed with 600 mg platinum activated charcoal (with stirring). After filtration through a membrane filter the mixture is evaporated and the residue is washed with diethylether.

Pale-yellow powder (substance D 20 975), M.P. 208°-209° C., (decomposition).
Yield: 600 mg.

Dihydroxy-Distearinato(1-Phenethyl-1-Methylethylenediamine)-Platinum(IV)

The corresponding distearinato complex (replacement of the two Cl by 2 stearic acid anions) is obtained as follows):

1 g stearinato-platinum(II) complex (substance D 21 393) is suspended in 30 ml $H_2O$ and 10 ml 35% $H_2O_2$ solution carefully added dropwise at 70° C. (vigorous foaming). The mixture is treated with 600 mg platinum active charcoal after 5 hours' stirring at 70° C., filtered over a membrane filter, evaporated and the residue is washed with ether.

Yellow powder (substance D 21 406), M.P. 200°-202° C. (decomposition).
Yield: 400 mg.

Dihydroxy-dineodecanato (1-Phenethyl-1-methylethylenediamine-platinum(IV)

1 g (0.001 Mol) neodecanato-platinum(II) complex (substance D 21 392) is oxidized in a manner analogous to the dihydroxydistearinato compound (see above) with 10 mg 35% $H_2O_2$ solution. Yellow product that hardens to a sticky mass.

Yield: 1.0 g (substance D 21 423).
No melting point.

EXAMPLE 23

(Further Examples For The Exchange Of Group X)

Preparation Of Lactate Complexes

The lactic acid used for this exchange reaction must be freshly distilled since polymeric esters could form during storage over a longer period of time.

The platinum complex with the anion X (for example X=Cl) is first converted to the appropriate diamine-dihydro-platinum(II) complex for example in the following manner:

5 mMol of platinum complex (for example chloro complex) are suspended in ca. 25 ml $H_2O$. This is done by alternately placing the batch into an ultrasonic bath for one hour and stirring for one hour, complex forming on the wall of the flask always being rinsed back into the suspension. An adequate suspension is achieved after this procedure has been repeated three to four times. A solution of 10 mMol (1.86 g) $AgNO_3$ in ca. 5 ml $H_2O$ is then added with exclusion of light. After the batch has been stirred for one week, the precipitated AgCl is filtered off as a pale-grey precipitate over a membrane filter frit. The dihydro complex remains in solution.

D,L-1-Benzyl-2,2-dimethylethylenediamine-L-lactato-platinum(II)

5 mMol (0.45 g) L-(+)-lactic acid are dissolved in 10 ml distilled water in order to serve as reservoir for the ion exchange column.

25 g strongly basic ion exchanger (Merck; Ion exchanger III; exchange capacity 4 mVal/g; that is 25 g=100 mVal, i.e. 10-fold excess compared to the platinum complex) are filled into a chromatographic column. The ratio of column diameter to column length should be 1:4 to 1:10.

In order to coat the ion exchange resin with $OH^-$, it is first flushed eight times with the resin volume of 2N NaOH. The pH of the eluate is then adjusted to a pH of ca. 9 by subsequent washing with $H_2O$.

Finally, the filtrate of the D,L-1-benzyl-2,2-dimethylethylenediamine-dihydro complex is brought to the column prepared in this manner and added dropwise to the stirred reservoir at a throughflow speed of ca. 2 cm/minute.

After addition has been completed, the mixture is stirred for a further 3-4 hours at 40° C.

To isolate the complexes the water first has to be totally removed. The glassy residue is then taken up with ca. 5 ml ethanol and the solution is reacted with 100 ml ether. A colorless, flocculant precipitate is obtained. While the precipitate is filtered off under nitrogen blanket, the filter cake should be suctioned dry as quickly as possible since it rapidly acquires a brown discoloration and begins to liquify when wet.

Yield: 67% (in relation to the chloro complex) colorless powder $C_{14}H_{22}N_2O_3Pt$ (molecular weight 461.4 g).

IR (KBr): 3200, 3080 $cm^{-1}$ (NH), 3060 (CH arom.), 2980 (CH aliph.), 1680, 1610 (C=O), 380 (PtO).

1H-NMR ($D_2O$, 250 MHz): $\alpha$=7.25-7.34 (m, 5H, phenyl), 4.35, 4.02, 3.57 (2m, 1H, CH), 2.83-2.93 (m, 1H, CH—N), 2.46-2.72 (m, 2H, $CH_2$-phenyl), 1.09-1.46 (m, 9H, $CH_3$).

| Analysis: | C | H | N |
|---|---|---|---|
| calculated: | 36.50 | 4.80 | 6.07 |
| found: | 36.34 | 5.04 | 5.84 |

The following lactato complexes are obtained in an analogous manner.

D,L-1-Benzyl-1-methylenediamine-L-lactato-platinum-(II)

Yield: 32% (in relation to the chloro complex) colourless powder $C_{13}H_{20}N_2O_3Pt$ (molecular weight 447.4 g).

IR (KBr): 3200, 3100 cm$^{-1}$ (NH), 3040 (CH arom.), 2980, 2940 (CH aliph.), 1750, 1610 (C=O), 370 cm$^{-1}$ (PtO).

1H-NMR (D$_2$O, 250 MHz): $\delta$ = 3.23–7.32 (m, 5H, phenyl), 3.98–4.02 (m, 1H, CH), 2.83–3.55, 2.38–2.62 (2m, 4H, CH$_2$-phenyl), CH$_2$-N), 1.14–1.35 (m, 6H, CH$_3$).

| Analysis: | C | H | N |
|---|---|---|---|
| calculated: | 34.90 | 4.51 | 6.26 |
| found: | 34.79 | 5.04 | 6.01 |

D,L-1-Benzyl-1-ethylethylenediamine-L-lactato-platinum(II)

Yield: 54% (in relation to the chloro complex) colorless powder $C_{14}H_{22}N_2O_3Pt$ (molecular weight 461.4 g).

IR (KRr): 3200, 3080 cm$^{-1}$ (NH), 3040 (CH arom.), 2980, 2940 (CH aliph.), 1730, 1610 (C=O), 760, 700 (PtO).

1-H-NMR (D$_2$O, 250 MHz): $\delta$ = 7.21 (m, 5H, phenyl), 4.34, 4.10, 3.99, 3.56 (4m, 1H, CH), 2.88–2.99, 2.41–2.55 (2m, 4H, CH$_2$-phenyl, CH$_2$-N), 1.46–1.76 (m, 2H, CH$_2$), 1.34, 1.22, 1.17, 1.10 (4d, 3H, $^3I$=6.9, CH), 0.91–0.96 (m, 3H, CH$_3$).

| Analysis: | C | H | N |
|---|---|---|---|
| calculated: | 36.44 | 4.81 | 6.07 |
| found: | 35.73 | 4.99 | 5.55 |

1,1-Dibenzylethylenediamine-L-lactato-platinum(II)

Yield: 32% (in relation to the chloro complex) colorless powder $C_{19}H_{24}N_2O_3Pt$ (molecular weight 5.23.5 g).

IR (KBr): 3200, 3080 cm$^{-1}$ (NH), 3040 (CH arom.), 2980 (CH aliph.), 1730, 1610 (C=O), 370 (PtO).

| Analysis: | C | H | N |
|---|---|---|---|
| calculated: | 40.78 | 5.04 | 5.00 |
| found: | 40.60 | 4.92 | 5.00 |

D,L-1-Benzyl-1-ethylethylenediamine glycolato-platinum(II)

Yield: 58% colorless powder.
$CH_{13}H_{20}N_2O_3Pt$ (molecular weight 447.4 g).

IR (KBr): 3220, 3110 cm$^{-1}$ (NH), 3040 (CH arom.), 2980, 2950 (CH aliph.), 1640 (CO), 370 (PtO).

1H-NMR (D$_2$O, 250 MHz): 7.31 (m, 5H, phenyl), 3.94 (AB, 2H, CH$_2$-O), 3.04–2.83, (m, 2H, CH$_2$-phenyl), 2.49, 2.47 (m, 2H, CH$_2$-N, 1.85–1.51 (m, 2H, CH$_2$), 1.08–0.96 (2t, 3H, CH$_3$).

| Analysis: | C | H | N |
|---|---|---|---|
| calculated: | 34.90 | 4.51 | 6.26 |
| found: | 34.44 | 4.82 | 5.35 |

D,L-1-Benzyl-1-ethylethylenediamine mandelato-platinum(II)

Yield: 47% colorless powder.
$C_{19}H_{24}N_2O_3Pt$ (molecular weight 5.23.5 g).

IR (KBr): 3220, 3220 cm$^{-1}$ (NH), 3060, 3040 (CH arom.), 2980, 2940 (CH aliph.), 1640 (CO), 360 (PtO).

1H-NMR (CD$_2$OD, 250 MHz): 7.72, 7.31 (2m, 10H, phenyl), 4.86, 4.88 (2s, 1H, CH-phenyl), 3.11, 2.96 (m, 2H, CH$_2$-phenyl), 2.51–2.43 (m, 2H, CH$_2$-N), 1.89–1.55 (m, 2H, CH$_2$), 1.07, 1.06 (2t, 3H, CH$_3$).

| Analysis: | C | H | N |
|---|---|---|---|
| calculated: | 43.59 | 4.63 | 5.35 |
| found: | 43.56 | 4.88 | 5.49 |

2-Amino-2-aminomethylindan-L-lactato-platinum(II)

Yield: 36% (in relation to the chloro complex) colorless powder.

$C_{13}H_{18}N_2O_3Pt$: (molecular weight 445.4 g).

IR (KBr): 3280, 3220 cm$^{-1}$ (NH), 3060 (CH aromatic), 2970, 2920 (CH aliphatic, 1590(NH), 320 (PtCl).

| Analysis: | C | H | N |
|---|---|---|---|
| calculated: | 32.40 | 4.61 | 5.81 |
| found: | 31.95 | 4.43 | 5.44 |

The exchange of the group X using other anionic groups or acids is for example carried out in a manner analogous to that described below.

EXAMPLE 24

(Examples for the cyclodextrin-platinum complex preparations)

Preparation of D,L-1-benzyl-2,2-dimethylethylenediamine dichloroplatinum(II) with α-cyclodextrin $1 \times 10^{-5}$ Mol (4.4 mg) of the previously mentioned platinum complex are dissolved in ca. 50 ml ethanol with gentle heating (30° C.). The double-equivalent amount of α-cyclodextrin, i.e. $2 \times 10^{-5}$ Mol (19mg) are dissolved in ca. 10 ml distilled water. Both solutions are combined and the solvent is removed is removed in a rotary evaporator.

The glassy residue is dried in a high vacuum ($10^{-4}$ Torr) and for example for the test on P 388 mouse leukaemia dissolved in 10 ml solvent mixture of polyethylene glycol 400 and 1.8% sodium chloride solution (1:1) in an ultrasonic bath.

EXAMPLE 25

(Example of the Preparation of Polyvinylpyrrolidone coprecipitates)

$1 \times 10^{-5}$ Mol D,L-1-benzyl-1-methylethylenediamine dichloro platinum(II) are dissolved in ca. 50 ml ethanol with heating (30° C.) 56 mg polyvinylpyrrolidone-10 (average molecular weight 10,000) are dissolved in 10 ml ethanol and added to the platinum complex solution. After removal of the solvent a yellow glassy residue is obtained that is dried in a high vacuum. To prepare the application solution this coprecipitate is for example dissolved in an ultrasonic bath in 10 ml of the solvent mixture polyethylene glycol 400/1.8% sodium chloride solution (1:1).

Preparation of C2-substituted benzylethylenediamine ligands of formula

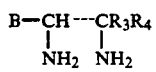

as well as of cyclic amine ligands as well as of C1-substituted benzylethylenediamine ligands which are substituted at the benzyl radical.

EXAMPLE 26

D,L-1-Benzyl-2,2-dimethylethylenediamine 9 mMol (1.8 g) Amino-azide D,L-1-phenyl-2-amino-3-azido-3-methyl butane are dissolved in ca. 30 ml ether and added dropwise with ice cooling to a suspension of 20 mMol (0.76 g) LiAlH$_4$ in 30 ml ether. After boiling under reflux for 4-5 hours, the mixture is allowed to cool and is hydrolyzed at 0°-5° C. with moist ether and a little water. The sludge-like hydrolysis product is suction filtered and the filtrate dried over Na$_2$SO$_4$.

After removal of the solvent, the residue is bulb-tube distilled in a high vacuum ($10^{-4}$ Torr) at ca. 90° C.

The residue from the hydrolysis is extracted overnight in a Soxhlet apparatus with 100 ml CH$_2$Cl$_2$. The extract is freed of solvent after drying and the residue is also distilled in a high vacuum at 90° C.

Yield: 50% colorless oil.
IR: see Table 1.

EXAMPLE 27

D,L-1-(4-chlorobenzyl)-2,2-dimethylethylenediamine

Method: analogous to Example 26, using 9 mMol (1.8 g) D,L-1-(4-chlorophenyl)-2-amino-3-azido-3-methyl butane. Bulb-tube distillation in a high vacuum ($10^{-4}$ Torr) at 120° C.

Yield: 54% colorless oil.
IR: see Table 1.

EXAMPLE 28

D,L-1-Benzyl-2,2-diethylethylenediamine

Method: analogous to Example 26, using 9 mMol (2.1 g) D,L-1-phenyl-2-amino-3-azido-3-ethyl-n-pentane. Bulb-tube distillation in a high vacuum ($10^{-4}$ Torr) at 90° C.

Yield: 90% colorless oil.
IR: see Table 1.

EXAMPLE 29

D,L-1-Benzyl-2,2-di-n-pentylethylenediamine

Method: analogous to Example 26, using 9 mMol (2.8 g) D,L-1-phenyl-2-amino-3-azido-3-n-pentyl-n-octane. Bulb-tube distillation in a high vacuum ($10^{-4}$ Torr) at 140° C.

Yield: 90% colorless oil.
IR: see Table 1.

EXAMPLE 30

D,L-1-Benzyl-2,2-dicyclohexylethylenediamine

Method: analogous to Example 26, using 9 mMol (2.8 g) D,L-1,1-dicyclohexyl-1-azido-2-amino-3-phenyl propane.
IR: see Table 1.
Preparation of the dihydrochloride 1.5 g diamine are dissolved in 10 ml ether and the solution is cooled down to −70° C. After brief introduction of HCl gas a yellowish precipitate is obtained which is filtered off, washed with ether and dried. The dihydrochloride is a pale yellow, hygroscopic powder.

EXAMPLE 31

D,L-1-Benzyl-2,2-diphenylethylenediamine

Method: analogous to Example 26, using 9 mMol (3.0 g) D,L-1,1-diphenyl-1-azido-2-amino-3-phenyl propane. Bulb-tube distillation in a high vacuum ($10^{-4}$ Torr) at 130° C.

Yield: 67% brown semisolid oil.
IR: see Table 1.

EXAMPLE 32

D,L-1-Benzyl-2,2-di(4-methoxyphenyl)ethylenediamine

Method: analogous to Example 26, using 9 mMol (83.2 g) D,L-1-di(4-methoxyphenyl)-1-azido-2-amino-3-phenyl propane. Bulb-tube distillation in a high vacuum ($10^{-4}$ Torr) at 200° C.

Yield: 30% semisolid oil.
IR: see Table 1.

EXAMPLE 33

D,L-1-(4-methoxybenzyl)-2,2-di(4-methoxyphenyl)ethylenediamine

Method: analogous to Example 26, using 9 mMol (3.8 g) D,L-1,1-di(4-methoxyphenyl)-1-azido-2-amino-3-(4-methoxyphenyl)propane. Cleaning by means of chromatography over a silica gel column (50 cm×5 cm). The substance is applied in toluene/ether (1:1). Using this elution agent a 1st zone is separated out and this is discarded. The diamine is finally washed off the column using methanol.

Yield: 20% yellow, semisolid oil.
IR: see Table 1.

EXAMPLE 34

D,L-1-Amino-1-aminomethyltetralin 69.7 mMol (2.6 g) LiAlH$_4$ are suspended in 70 ml tetrahydrofuran. 34.8 mMol (6.0 g) D,L-1-amino-1-cyanotetralin in 30 ml tetrahydrofuran are added dropwise to this suspension with ice cooling.

After removal of the ice bath the mixture is refluxed overnight. Hydrolysis occurs by adding 20 ml water dropwise with ice cooling. The slurry-like hydrolysis product is filtered off and extracted overnight with 250 ml tetrahydrofuran in a Soxhlet apparatus. The filtrate and the extraction solution are combined and the solvent is drawn off. A brown oil is obtained which is bulb-tube distilled in a high vacuum ($10^{-4}$ Torr). The by-product is distilled over at 60° C. The diamine is obtained at a temperature of 90° C.

Yield: 18%, colorless oil.
$C_{11}H_{16}N_2$ (molecular weight 176.3 g).
IR: see Table 1.

EXAMPLE 35

D,L-4-Amino-4-aminomethylchroman

Method: by analogy with Example 26 using 20.1 mMol (3.5 g) D,L-4-amino-4-cyanochroman.

Bulb-tube distillation ($10^{-4}$ Torr): 1st fraction at 70° C. (by-product); 2nd fraction at 100° C. (diamine).
Yield: 27%, yellow oil.
$C_{10}H_{14}N_2O$ (molecular weight 178.2 g).
IR: see Table 1.

EXAMPLE 36

D,L-2-Amino-2-aminomethyldecalin

Method: by analogy with Example 26 using 62.8 mMol (11.2 g) D,L-2-amino-2-cyanodecalin.

Bulb-tube distillation ($10^{-4}$ Torr): 1st fraction at 60° C. (by product); 2nd fraction at 100° C. (diamine).
Yield: 10%, colourless oil.
$C_{11}H_{22}N_2$ (molecular weight 182.3 g).
IR: see Table 1.

EXAMPLE 37

D,L-1-(p-Methoxy)benzyl-1-methylethylenediamine

Method: by analogy with Example 26 using 33.6 mMol (6.4 g) D,L-1-(p-methoxy)phenyl-2-amino-2-cyanopropan.

Bulb-tube distillation ($10^{-4}$ Torr): 1st fraction at 65° C. (by-product); 2nd fraction at 90° C. (diamine).
Yield: 15%, colorless oil.
$C_{11}H_{18}N_2O$ (molecular weight 194.3 g).
IR: see Table 1.

EXAMPLE 38

2-Amino-2-aminomethyltetralin

Method: by analogy with Example 26 using 31.0 mMol (5.9 g) tetralin-2-amino-2carboxylic acid amide.
Bulb-tube distillation.
Boiling point: 110° C. ($10^{-4}$ Torr).
Yield: 45%, colorless oil.
$C_{11}H_{11}N_2$ (molecular weight 176.3 g).
IR: see Table 1.

EXAMPLE 39

1-(p-Hydroxy)benzyl-1-methylethylenediamine 7.21 mMol (1.4 g) 1-(p-Methoxy)benzyl-1-methylethylenediamine are dissolved in 150 ml methylene chloride and cooled to −78° C. 43.21 mMol (4.1 ml) $BBr_3$ are then added dropwise at the same temperature and stirred for one hour at −78° C. and then for 20 hours at 20° C. The mixture is hydrolyzed at 0° C. with 30 ml methanol, during which part of the product crystallizes out. After distillation of the solvent the product is obtained quantitatively as a colorless solid.

Yield: quantitative, colorless solid.
$C_{10}H_{16}N_2O$ (molecular weight 180.2 g).
IR: see Table 1.

TABLE 1

| Example No. | IR data of the C2-substituted benzylethylenediamines (film) [cm$^{-1}$] | | | | | |
|---|---|---|---|---|---|---|
| | ν(NH) sym. and asym. | νCH arom. | νCH | δ(NH) aliph. | ν(C=C) sym. and asym. | δCH arom. out of plane |
| 26 | 3390m<br>3300m | 3020m | 2980s | 1600s | 1500s<br>1450s | 700s<br>750s |
| 27 | 3360m<br>3280m | 3040w | 2980s<br>2960m | 1600s | 1500s<br>1450m | 840m<br>810s |
| 28 | 3380m<br>3320m | 3040s | 2980s<br>2960s | 1610s | 1500s<br>1460s | 700s<br>750s |
| 29 | 3400m<br>3320m | 3040s | 2980s<br>2960s | 1610s | 1500s<br>1460s | 710s<br>750s |
| 30 | 3340m | 3040m | 2940s<br>2860s | 1660m | 1500m<br>1460s | 700s<br>730m |
| 31 | 3380m<br>3300m | 3040s<br>3060s | 2920s<br>2860m | 1610s | 1500s<br>1450s | 700s<br>750s |
| 32 | 3400m<br>3340m | 3020s<br>3040s | 2960s<br>2920s | 1620s<br>1620s | 1510s<br>1450s | 700s<br>750 |
| 33 | 3360b | 3020m<br>3040m | 2960s<br>2920m | 1620s<br>1580m | 1510s<br>1470m | 830s |
| 34 | 3370sb<br>3300sb | 3060m<br>3020m | 2930s<br>2860s | 1600s | 1480s<br>1440s | 740s |
| 35 | 3380sb<br>3300sb | 3080m<br>3040m | 2950s<br>2880s | 1620s<br>1580s | 1500s<br>1460s | 770s |
| 36 | 3280sb | | 2900s<br>2860s | 1600s | | |
| 37 | 3360sb<br>3280sb | 3040w<br>3000w | 2910w<br>2820s | 1615s<br>1590s | 1510s<br>1565s | 840s |
| 38 | 3100–<br>3400sb | 3020w | 2920s<br>2850m | 1600s | 1500s<br>1460s | 740s |
| 39<br>IR in KBr | 3360sb<br>3310sb<br>3530 (OH) sb | 3030w<br>3010w | 2920w<br>2850w | 1620s<br>1585s | 1525s | 835s |

Preparation of C1-substituted benzylethylenediamine ligands of the formula

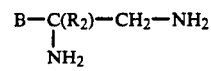

EXAMPLE 40

D,L-1-Benzyl-1-phenylethylenediamine

Method: by analogy with Example 26 using 9 mMol (2.3 g) D,L-1,2-diphenyl-2-azido-3-aminopropan. Bulb-tube distillation in a high vacuum ($10^{-4}$ Torr) at 180° C.
Yield: 83% colorless oil.
IR: see Table 2.

EXAMPLE 41

D,L-1-Benzyl-1-methylethylenediamine 0.4 Mol (15.2 g) $LiAlH_4$ are prepared as a suspension in ca.100 ml tetrahydrofuran. 0.1 Mol (16.02 g) D,L-1-Phenyl-2-amino-2-cyanopropan are dissolved in 150 ml tetrahydrofuran and added dropwise using a dropping funnel to the $LiAlH_4$ suspension with ice cooling. After addition has been completed, the ice bath is removed and the mixture is boiled under reflux for 15 hours.

For purposes of hydrolysis 1.6 Mol (28.8 ml) distilled water are carefully added dropwise with ice cooling and with vigorous stirring.

The slurry-like hydrolysis product is filtered off and extracted in a Soxhlet apparatus for 15 hours with 250 ml tetrahydrofuran.

The residue which is obtained after distillation of the solvent is bulb-tube distilled in a high vacuum ($10^{-4}$ Torr). The fraction of the by-product can be totally distilled off at temperature of 70° C.

The diamine is finally distilled over at 100° C.
Yield: 42% colorless oil.
IR: see Table 2.

EXAMPLE 42

D,L-1-Benzyl-1-ethylethylenediamine

Method: by analogy with Example 41 using 0.1 Mol (17.4 g) D,L-1-phenyl-2-amino-2-cyanobutane.

Bulb-tube distillation in a high vacuum ($10^{-4}$ Torr): 1st fraction at 60° C. (by-product); 2nd fraction at 95° C. (diamine).

Yield: 28%, colorless oil.
IR: see Table 2.

EXAMPLE 43

1,1-Dibenzylethylenediamine

Method: by analogy with Example 41 using 0.1 Mol (23.6 g) 1,3-diphenyl-2-amino-2-cyanopropan.

Bulb-tube distillation in a high vacuum ($10^{-4}$ Torr): 1st fraction at 100° C. (by-product); 2nd fraction at 150° C. (diamine).

Yield: 32%, slightly yellowish oil.
IR: see Table 2.

TABLE 2

IR data of the Cl-substituted benzylethylenediamines (film) [cm$^{-1}$]

| Example No. | ν(NH) sym. and asym. | CH arom. | CH aliph. | δ(NH) | ν(C=C) sym. and asym. | CH arom. out of plane |
|---|---|---|---|---|---|---|
| 40 | 3390m | 3040 | 2920m | 1610s | 1500s | 710s |
|    | 3300m |      | 2860m | 1590w | 1460s | 760s |
| 41 | 3290m | 3020s | 2920s | 1610s | 1500s | 710s |
|    | 3300m |       | 2860s | 1590m | 1460s | 760m |
| 42 | 3390m | 3020s | 2920s | 1610s | 1500s | 710s |
|    | 3300  |       | 2860s | 1590m | 1460s | 760m |
| 43 | 3390m | 3040s | 2920s | 1610s | 1500s | 710s |
|    | 3300m |       | 2860s | 1590m | 1460s | 760m |

Preparation of cyclic benzylethylenediamines

EXAMPLE 44

2-Amino-2-aminomethylindane

Method: by analogy with Example 41 using 0.1 Mol (15.8 g) 2-amino-2-cyanoindane.

Bulb-tube distillation in a high vacuum ($10^{-4}$ Torr) at 150° C.

Yield: 46%, colorless solid.

IR (KBr): [cm$^{-1}$] see following table:

| ν(NH) sym. and asym. | CH arom. | CH aliph. | δ(NH) | ν(C=C) sym. and asym. | CH arom. out of plane |
|---|---|---|---|---|---|
| 3320m | 3080m | 2900s | 1610m | 1490s | 750s |
| 3240m | 3020m | 2840m | 1580m | 1440s | 710w |

EXAMPLES OF GALENIC FORMULATIONS

Examples of capsules 1 kg of the compound of Example 21 in the form of the L-lactic acid complex, 625 g microcrystalline cellulose and 11 g highly disperse silicon dioxide are passed through a sieve of mesh size 0.8 mm and homogenized. 39 g magnesium stearate (sieved 0.8 mm) are then added to this mixture and mixing continued for a further one minute.

To prepare the capsules, the capsule mass is dispensed in known manner in a capsule machine equipped with size 00 molds into hard gelatin capsules of size 00. The filled amount per capsule is 670 mg, corresponding to 400 mg active substance.

Examples for a lyophilizate with skeleton former 20 g of the compound of Example 21 and 94 g mannitol are dissolved with stirring in 900 ml sterile water suitable for injection purposes. The mixture is then made up to 1 liter with sterile water suitable for injection purposes.

This solution is sterile filtered through a membrane filter of 0.2 μm pore width under aseptic conditions and dispensed in 2 ml portions into 10 ml injection vials of hydrolytic class I. The vials are closed with a freeze-drying stopper and lyophilized in an appropriate installation. After drying, the vials are sealed in the installation with gassing with sterile, dry nitrogen. The stoppers are secured with a cap.

For intravenous use the lyophilizate is dissolved in 4 ml water for injection purposes.

Each injection vial contains 40 mg active substance, 1 ml of solution contains 10 mg active substance.

Example for a lyophilizate without skeleton former 20 g of the compound of Example 21 are dissolved with stirring in 3900 ml sterile water suitable for injection purposes. The mixture is then made up to 4 liters with sterile water suitable for injection purposes.

This solution is sterile filtered through a membrane filter of 0.22 μm pore width under aseptic conditions and dispensed in 8 ml portions into 30 ml injection vials of hydrolytic class I. The vials are closed with a freeze-drying stopper and lyophilized in an appropriate apparatus. After drying, the vials are sealed in the apparatus with gassing with sterile, dried nitrogen. The stoppers are secured with a cap. For intravenous use the lyophilizate is dissolved in 8 ml water for injection purposes.

Each injection vial contains 40 mg active substance, 1 ml of solution contains 5 mg active substance.

Example of a phospholipid dispersion 20 g of the compound of Example 21, in which two stearic acid anions are present in place of the two Cl$^-$, are dissolved in 4 kg CH$_2$Cl$_2$ with stirring. 399.8 g soya lecithin and 0.2 g α-tocopherol are then added with stirring. The organic solvent is removed in a vacuum (for example using a rotary evaporator). The lipid film is reacted with 9.58 kg 0.9% NaCl solution, shaken for 3 hours and filtered consecutively under aseptic conditions through 0.8 and 0.2 μm membrane filters. The liquid is filled under aseptic conditions in 2 g portions into hydrolytic class I injection vials. The vials are sealed with injection stoppers.

Each injection vial contains 40 mg active substance in 2 g phospholipid dispersion.

What is claimed is:

1. Platinum (II or IV) complexes of the general formula

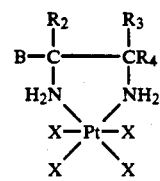

where B represents a phenyl-$C_1$-$C_4$-alkyl radical which is optionally substituted in the phenyl nucleus by the radical $R_1$ and $R_1$ is hydrogen, halogen, trihalogen methyl, $C_1$-$C_6$-alkyl, hydroxy, $C_1$-$C_6$-alkoxy or $C_2$-$C_6$-alkanoyloxy or where B together with the structural part $H_2N$—$CR_2<$ forms a tetrahydroisoquinoline radical, if B contains benzyl and $R_2$ hydrogen and the benzyl radical in the 2-position contains the $CH_2$-radical or where B together with the structural part —$CR_2<$ represents a tetrahydronaphthyl radical in which one $CH_2$ group is optionally replaced by oxygen, or where B together with the structural part —$CR_2<$ represents a decahydronaphthyl radical or an indanyl radical; $R_2$ represents hydrogen, $C_1$-$C_6$-alkyl, phenyl or phenyl-$C_1$-$C_4$-alkyl, it also being possible for the phenyl ring of this group $R_2$ to be substituted by hydroxy, $C_1$-$C_4$-alkoxy, $C_1$-$C_4$-alkyl, $C_2$-$C_6$-alkanoyloxy or halogen;

the radicals $R_3$ and $R_4$ are the same or different and represent hydrogen, $C_1$-$C_{12}$-alkyl, $C_3$-$C_8$-cycloalkyl, phenyl which is optionally substituted by $C_1$-$C_6$-alkoxy and, if B is a benzyl radical (optionally substituted as stated), at least one of the radicals $R_2$, $R_3$ and $R_4$ is not hydrogen and X stands for the equivalent of a physiologically acceptable anion or X can also be a water molecule, where in the latter case the missing negative charge is saturated by a corresponding physiologically acceptable acid anion, where in the case of platinum((II) complexes, two of the groups X are absent.

2. A complex selected from the group consisting of D,L-1-(4-Chlorobenzyl)-2,2-dimethylethylenediamine-dichloroplatinum (II), D,L-1-Benzyl-2,2-dimethylethylenediamine-dichloro-platinum (II), D,L-1-Benzyl-2,2-diethylene-diamine-dichloro-platinum (II), D,L-1-Benzyl-2,2-dipentylethylenediamine-dichloro-platinum (II), D,L-1-Benzyl-2,2-dichlorohexylethylene-diamine-dichloro-platinum (II), D,L-1-Benzyl-2,2-diphenylethylenediamine-dichloro-platinum (II), D,L-1-Benzyl-2,2-di-(4-methoxyphenyl) ethylenediamine-dichloro-platinum (II), D,L-1-(4-Methoxybenzyl)-2,2-di-(4-methoxyphenyl)ethylene diamine-dichloro-platinum (II), D,L-1-Benzyl-1-phenylethylenediamine-dichloro-platinum (II), D,L-1-Benzyl-1-methyl-ethylenediamine-dichloro-platinum (II), D,L-1-Benzyl-1-ethylethylenediamine-dichloro-platinum (II), 1,1-Dibenzyl-1-ethylethylenediamine-dichloro-platinum (II), 2-amino-2-aminomethylindane-dichloro-platinum (II), D,L-3-Aminomethyl-1,2,3,4-tetrahydroisoquinoline-dichloroplatinum (II), D,L-1-amino-1-aminomethyltetralin-dichloroplatinum (II), D,L-1-amino-4-aminomethyl-chroman-dichloroplatinum (II), D,L-2-amino-2-aminomethlydecalin-dichloroplatinum (II), D,L-1-(p-methoxy)benzyl-1-methylethylenediamine-dichloro-platinum (II), D,L-2-amino-2-aminomethyltetralin-dichloroplatinum (II), 1-(p-hydroxy)-benzyl-1-methylethylenediamine-dichloro-platinum (II), Dichloro-(1-phenyl-1-methyl-ethylene-diamine)-platinum (II), Glycolato-(1-phenyl-1-methyl-ethylene-diamine)-platinum (II), D-lacto-(1-phenyl-1-methyl-ethylene-diamine)-platinum (II), L-lacto-(1-phenyl-1-methyl-ethylene-diamine)-platinum (II), stearinato-(1-phenyl-1-methyl-ethylene-diamine)-platinum (II), neodecanato-(1-phenyl-1-methyl-ethylene-diamine)-platinum (II), ω-phenyloctadecanato(ω-phenylstearinato)-(1phenyl-1-methyl-ethylene-diamine)-platinum (II), sulphato-(1-phenyl-1-methyl-ethylene-diamine)-platinum (II), nitrolotris (methylphosphonato)-1-phenyl-1methylethylene-diamine)-platinum (II), Dichloro-dihydroxy-(1-phenethyl-1-methylethylenediamine)-platinum (IV), Dihydroxy-distearinato-(1-phenylethyl-1-methylethylenediamine-platinum (IV), Dihydroxy-dineodecanato-(1-phenylethyl-1-methylethylenediamine)-platinum (IV), D,L-1-Benzyl-2,2-dimethylethylenediamine-L-lacto-platinum (II), D,L-1-benzyl-1-methylethylenediamine-L-lactato-platinum, D,L-1-benzyl-1-ethylethylenediamine-L-lactato-platinum (II), 1,1-Dibenzylethylenediamine-L-lactato-platinum (II), D,L-1Benzyl-1-ethylethylene-diamine-glycolatoplatinum (II), D,L-1-Benzyl-1-ethylethylene-diamine-mandelato-platinum (II), 2-amino-2-aminomethylindan-L-lactato-platinum (II).

3. A complex as set forth in claim 1 in which
B is selected from the class consisting of phenyl-$C_1$-alkyl- or phenyl-$C_2$-alkyl-, which is optionally substituted by $R_1$ in the phenyl ring, in which $R_1$ is selected from the class consisting of hydrogen, halogen, hydroxy and methoxy, in which the substituents $R_3$ and $R_4$ may be the same or different and are selected from the class consisting of hydrogen, methyl, ethyl and phenyl, or in which
B forms, together with $H_2N$—$CR_2$, a tetrahydroisoquinoline, and in which x is a pharmaceutically acceptable anion.

* * * * *